(12) United States Patent
Scheller et al.

(10) Patent No.: US 11,707,192 B2
(45) Date of Patent: Jul. 25, 2023

(54) EYE-TRACKING USING LASER DOPPLER INTERFEROMETRY

(71) Applicant: META PLATFORMS TECHNOLOGIES, LLC, Menlo Park, CA (US)

(72) Inventors: Maik Andre Scheller, Redmond, WA (US); Jonathan Robert Peterson, Woodinville, WA (US); Joseph S. Corry, Seattle, WA (US); Liliana Ruiz Diaz, Redmond, WA (US); Andrew John Ouderkirk, Redmond, WA (US)

(73) Assignee: META PLATFORMS TECHNOLOGIES, LLC, Menlo Park, CA (US)

( * ) Notice: Subject to any disclaimer, the term of this patent is extended or adjusted under 35 U.S.C. 154(b) by 405 days.

(21) Appl. No.: 16/918,229

(22) Filed: Jul. 1, 2020

(65) Prior Publication Data
US 2022/0000362 A1    Jan. 6, 2022

(51) Int. Cl.
*A61B 3/113* (2006.01)
*A61B 3/00* (2006.01)
(Continued)

(52) U.S. Cl.
CPC .............. *A61B 3/113* (2013.01); *A61B 3/005* (2013.01); *A61B 3/0008* (2013.01);
(Continued)

(58) Field of Classification Search
CPC ..... A61B 3/113; A61B 3/0008; A61B 3/0025; A61B 3/005; A61B 2562/046;
(Continued)

(56) References Cited

U.S. PATENT DOCUMENTS 10,832,051 B1 * 11/2020 Trail ...................... G06V 40/19
10,890,823 B1 *  1/2021 Jiang ...................... C09K 19/04
(Continued)

OTHER PUBLICATIONS

Office Action dated Jan. 13, 2023 for European Application No. 21175837.0, filed May 26, 2021, 10 pages.
(Continued)

*Primary Examiner* — Mohammed A Hasan
(74) *Attorney, Agent, or Firm* — Morgan, Lewis & Bockius LLP

(57) ABSTRACT

An eye-tracking device includes an optical device that includes a light source with an optical cavity and a light sensor. The light source is positioned to output coherent light toward an eye of a user and receive at least a portion of the coherent light back from the eye of the user as feedback light. The feedback light enters the optical cavity and causes modulation of an intensity of the coherent light. The light sensor is optically coupled with the light source for detecting the modulated intensity of the coherent light and generating one or more signals based on the detected intensity of the coherent light. The eye-tracking device also includes one or more processors that are coupled to the optical device for determining, from the one or more signals, movement information of the eye. A method of detecting movement of an eye using the eye-tracking device is also disclosed.

19 Claims, 27 Drawing Sheets

(51) Int. Cl.
  *G02B 27/01* (2006.01)
  *G06F 3/01* (2006.01)
(52) U.S. Cl.
  CPC ........ *A61B 3/0025* (2013.01); *G02B 27/0172* (2013.01); *G06F 3/013* (2013.01); *A61B 2562/046* (2013.01); *G02B 2027/0178* (2013.01)
(58) Field of Classification Search
  CPC ........ G02B 27/0172; G02B 2027/0178; G02B 27/0093; G06F 3/013; G01B 9/02045; G01B 9/02092
  USPC ........................................................ 351/210
  See application file for complete search history.

(56) References Cited

U.S. PATENT DOCUMENTS

| | | | |
|---|---|---|---|
| 2017/0109562 A1* | 4/2017 | Shroff | G09G 3/36 |
| 2020/0026350 A1 | 1/2020 | Eash et al. | |
| 2020/0064641 A1* | 2/2020 | Lam | G02B 27/0179 |

OTHER PUBLICATIONS

Perchoux J., et al., "Photodiode-Free Doppler Velocimeter based on Self-Mixing Effect in Commercial VCSELs," IEEE Sensors, 2008, pp. 290-293.
Pruijmboom A., et al., "VCSEL-Based Miniature Laser-Doppler Interferometer," Springer Series in Optical Sciences, Oct. 2013, 7 pages.

\* cited by examiner

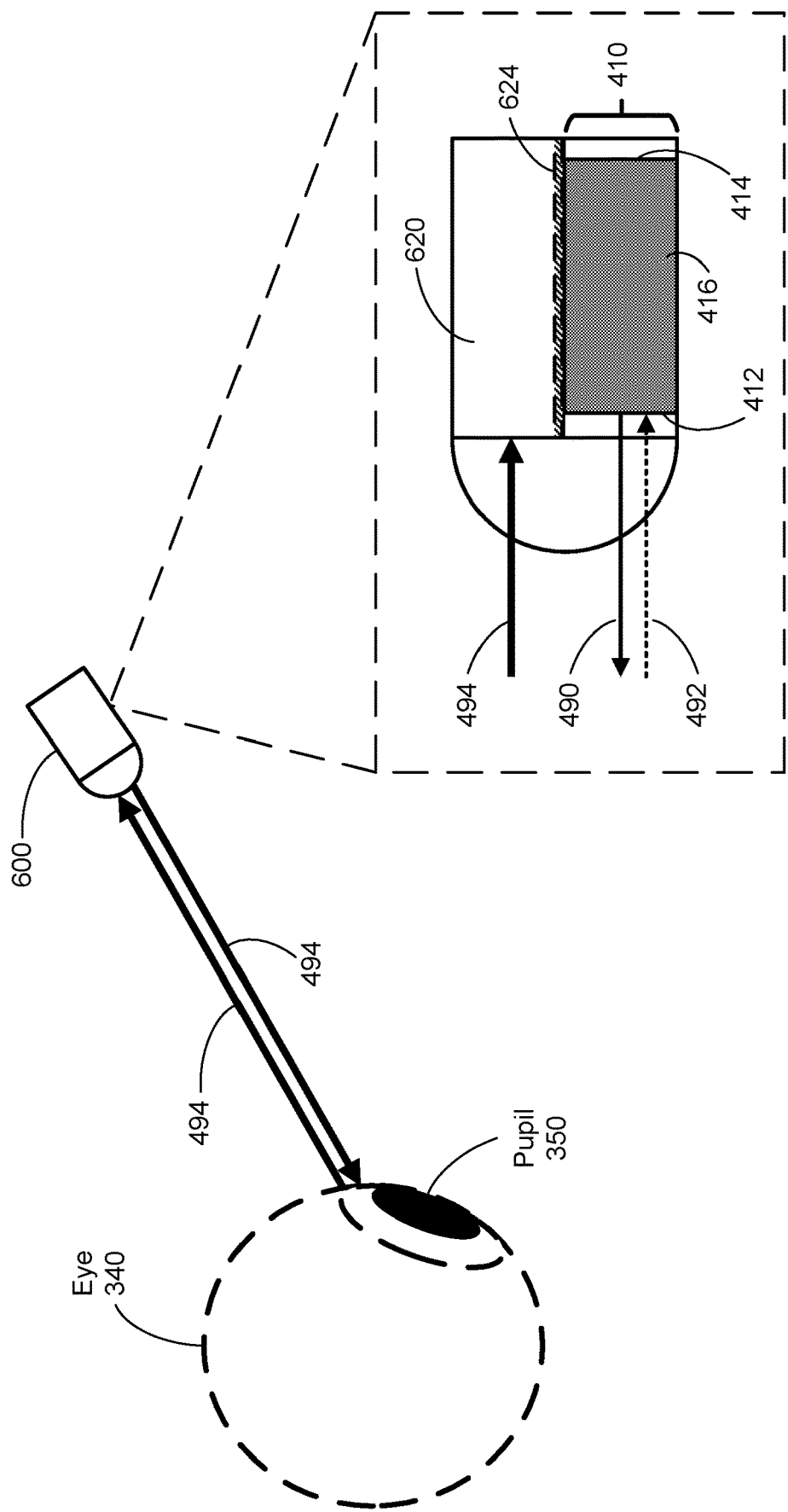

1400

```
┌─────────────────────────────────────────────────────────────────┐
│ 1410 Output first coherent light from a first light source of  │
│ a first optical device toward an eye. The first light source    │
│ has a first cavity and a first light sensor.                    │
│  ┌ ─ ─ ─ ─ ─ ─ ─ ─ ─ ─ ─ ─ ─ ─ ─ ─ ─ ─ ─ ─ ─ ─ ─ ─ ─ ─ ─ ─ ┐  │
│    1412 Change, with an electrical source coupled to the       │
│  │ first light source, an electrical current provided to the │  │
│    first light source in accordance with a predefined          │
│  │ non-uniform pattern.                                      │  │
│  └ ─ ─ ─ ─ ─ ─ ─ ─ ─ ─ ─ ─ ─ ─ ─ ─ ─ ─ ─ ─ ─ ─ ─ ─ ─ ─ ─ ─ ┘  │
└─────────────────────────────────────────────────────────────────┘
                                │
                                ▼
┌─────────────────────────────────────────────────────────────────┐
│ 1420 Receive, at the first optical device, at least a portion   │
│ of the first coherent light back from the eye as feedback       │
│ light. The feedback light enters the first optical cavity and   │
│ causes modulation of an intensity of the first coherent light.  │
└─────────────────────────────────────────────────────────────────┘
                                │
                                ▼
┌─────────────────────────────────────────────────────────────────┐
│ 1430 Detect the modulated intensity of the first coherent       │
│ light with the first light sensor.                              │
└─────────────────────────────────────────────────────────────────┘
                                │
                                ▼
┌─────────────────────────────────────────────────────────────────┐
│ 1440 Determine movement information of the eye based on at      │
│ least the modulated intensity of the first coherent light       │
│ detected with the first light sensor.                           │
└─────────────────────────────────────────────────────────────────┘
                                │
                                ▼
                              ( A )
```

1450 Output second coherent light from a second light source of a second optical device toward the eye. The second light source has a second optical cavity and a second light sensor.

---

1460 Receive, at the second optical device, at least a portion of the second coherent light back from the eye as feedback light. The feedback light enters the second optical cavity and causes modulation of an intensity of the second coherent light.

---

1470 Detect the modulated intensity of the second coherent light with the second light sensor. The movement information is also determined based on the modulated intensity of the second coherent light detected with the second light sensor.

Figure 14B

EYE-TRACKING USING LASER DOPPLER INTERFEROMETRY

TECHNICAL FIELD

This relates generally to display devices, and more specifically to eye-tracking in head-mounted display devices.

BACKGROUND

Head-mounted display devices (also called herein head-mounted displays) are gaining popularity as means for providing visual information to a user. For example, the head-mounted display devices are used for virtual reality and augmented reality operations. Eye tracking allows the head-mounted display devices to determine a user's gaze and provide visual information based on the user's gaze direction.

SUMMARY

Accordingly, there is a need for an eye-tracking system in a head-mounted display device that is accurate, light, compact, and cost-effective.

The systems and methods disclosed in this description use a Doppler-interferometer method to track the movement of the eye without any image processing or imaging requirements. Thus, the use of additional optical components such as external cameras are not required to provide accurate eye-tracking information thereby reducing the size and cost of the eye-tracking system. Additional computation steps such as background filtering, which are sometimes employed in imaging-based eye-tracking systems, are also eliminated thereby reducing computation cost and power consumption of the eye-tracking system.

In accordance with some embodiments, an eye-tracking device includes a first optical device and one or more processors coupled to the first optical device. The first optical device includes a first light source and a first light sensor that is optically coupled to the first light source. The first light source has a first optical cavity. The first light source is positioned to output first coherent light toward an eye of a user and to receive at least a first portion of the first coherent light back from the eye of the user as feedback light. The feedback light enters the first optical cavity and causes modulation of an intensity of the first coherent light. The first light sensor is configured to detect the modulated intensity of the first coherent light and generate one or more first signals based on the detected intensity of the first coherent light. The one or more processors is configured to determine, from the one or more first signals, movement information of the eye of the user.

In accordance with some embodiments, a head-mounted display device includes an eye-tracking device and a display configured to transmit one or more images to an eye of a user. The eye-tracking device includes a first optical device and one or more processors coupled to the first optical device. The first optical device includes a first light source and a first light sensor that is optically coupled to the first light source. The first light source has a first optical cavity. The first light source is positioned to output first coherent light toward an eye of a user and to receive at least a first portion of the first coherent light back from the eye of the user as feedback light. The feedback light enters the first optical cavity and causes modulation of an intensity of the first coherent light. The first light sensor is configured to detect the modulated intensity of the first coherent light and generate one or more first signals based on the detected intensity of the first coherent light. The one or more processors is configured to determine, from the one or more first signals, movement information of the eye of the user.

In accordance with some embodiments, a method of detecting a movement of an eye of a user includes outputting first coherent light from a first light source of a first optical device toward the eye. The first light source has a first optical cavity and the first optical device also includes a first light sensor. The method also includes receiving, at the first optical device, at least a portion of the first coherent light back from the eye as feedback light, whereby the feedback light enters the first optical cavity and causes modulation of an intensity of the first coherent light. The method further includes detecting the modulated intensity of the first coherent light with the first light sensor and determining movement information of the eye based on at least the modulated intensity of the first coherent light detected with the first light sensor.

Thus, the disclosed embodiments provide lightweight and compact eye-tracking systems that provide accurate eye-tracking information.

BRIEF DESCRIPTION OF THE DRAWINGS

For a better understanding of the various described embodiments, reference should be made to the Description of Embodiments below, in conjunction with the following drawings in which like reference numerals refer to corresponding parts throughout the figures.

FIGS. 6A-6C are schematic diagrams illustrating a horizontally integrated optical device in accordance with some embodiments.

FIGS. 14A and 14B are flow diagrams illustrating a method of providing active zonal illumination in accordance with some embodiments.

Figure 1:
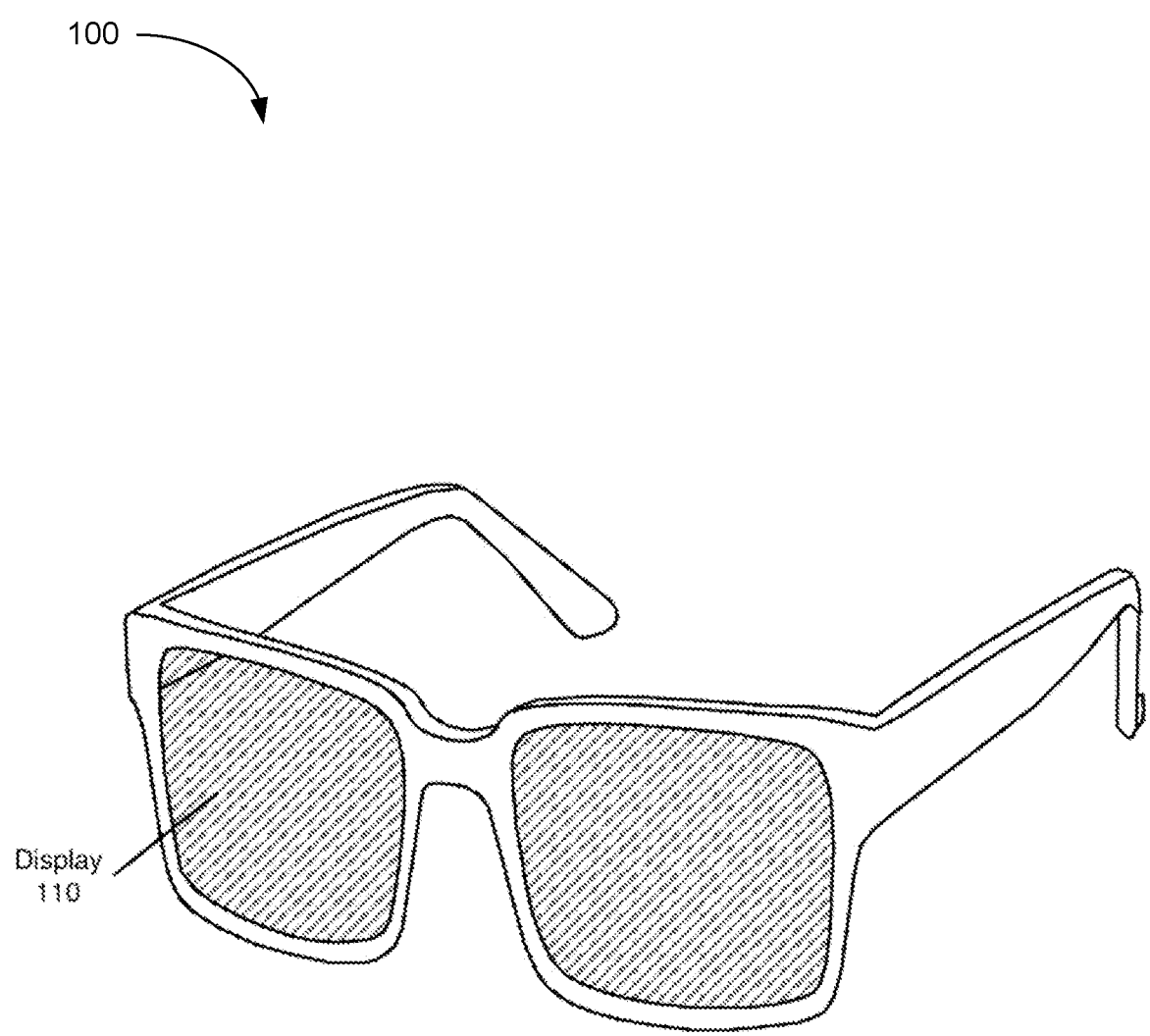
FIG. 1 is a perspective view of a display device in accordance with some embodiments.

These figures are not drawn to scale unless indicated otherwise.

DETAILED DESCRIPTION

There is a need for eye-tracking systems devices that are accurate, lightweight, and compact.

The present disclosure provides eye-tracking devices that provide accurate eye-tracking information in a compact footprint. The eye-tracking device includes an optical device that is configured to determine position and movement information of a user's eye using interferometric measurements. This eliminates the need for using imaging devices (e.g., a camera) for eye tracking. However, in some configurations, the disclosed eye-tracking devices may be used in conjunction with imaging devices to complement the imaging devices in eye tracking.

Reference will now be made to embodiments, examples of which are illustrated in the accompanying drawings. In the following description, numerous specific details are set forth in order to provide an understanding of the various described embodiments. However, it will be apparent to one of ordinary skill in the art that the various described embodiments may be practiced without these specific details. In other instances, well-known methods, procedures, components, circuits, and networks have not been described in detail so as not to obscure other aspects of the embodiments.

It will also be understood that, although the terms first, second, etc. are, in some instances, used herein to describe various elements, these elements should not be limited by these terms. These terms are used only to distinguish one element from another. For example, a first reflector could be termed a second reflector, and, similarly, a second reflector could be termed a first reflector, without departing from the scope of the various described embodiments. The first reflector and the second reflector are both light reflectors, but they are not the same reflector.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof. The term "exemplary" is used herein in the sense of "serving as an example, instance, or illustration" and not in the sense of "representing the best of its kind."

FIG. 1 illustrates display device 100 in accordance with some embodiments. In some embodiments, display device 100 is configured to be worn on a head of a user (e.g., by having the form of spectacles or eyeglasses, as shown in FIG. 1) or to be included as part of a helmet that is to be worn by the user. When display device 100 is configured to be worn on a head of a user or to be included as part of a helmet, display device 100 is called a head-mounted display. Alternatively, display device 100 is configured for placement in proximity of an eye or eyes of the user at a fixed location, without being head-mounted (e.g., display device 100 is mounted in a vehicle, such as a car or an airplane, for placement in front of an eye or eyes of the user). As shown in FIG. 1, display device 100 includes display 110. Display 110 is configured for presenting visual contents (e.g., augmented reality contents, virtual reality contents, mixed reality contents, or any combination thereof) to a user.

Figure 2:
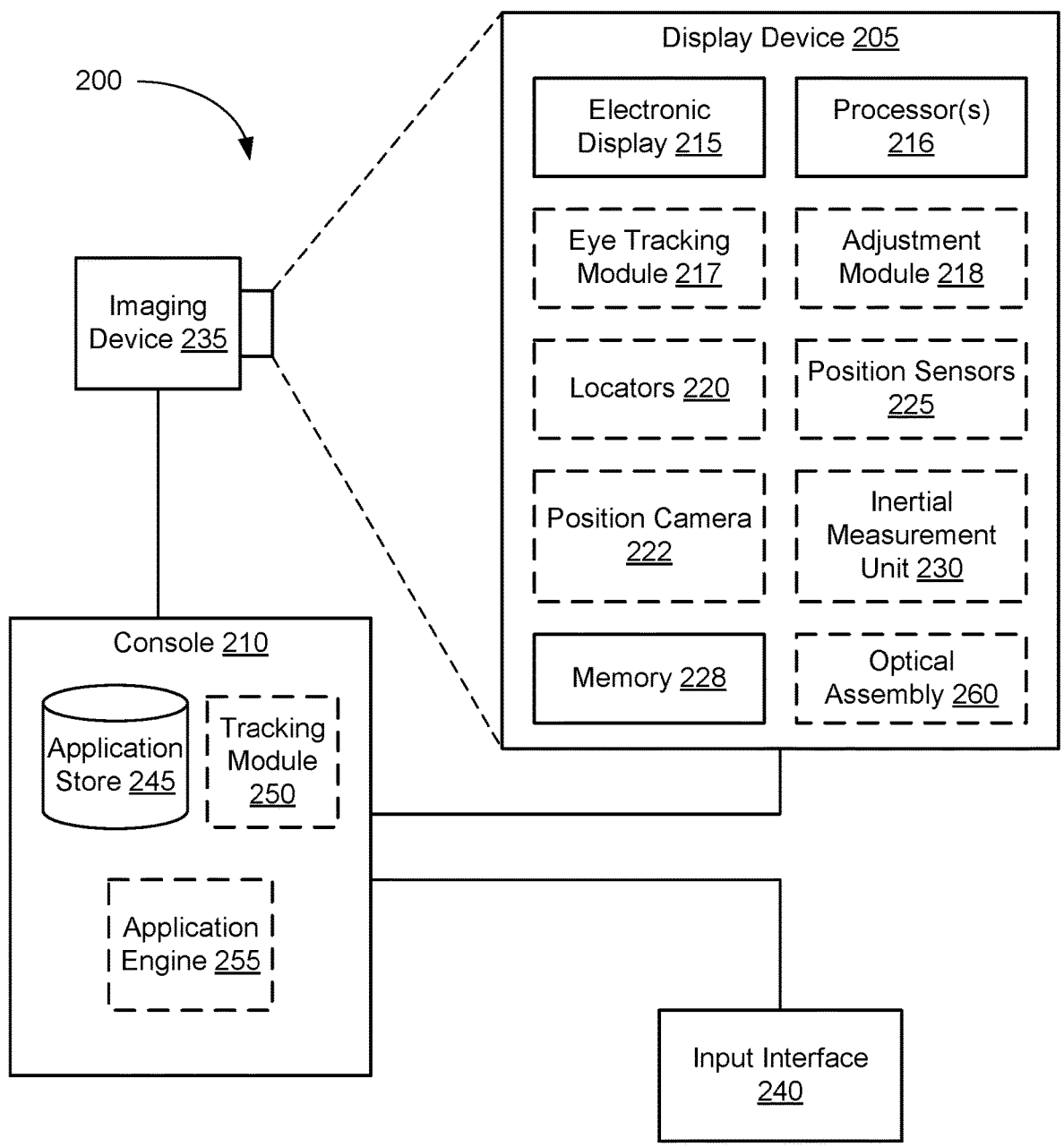
FIG. 2 is a block diagram of a system including a display device in accordance with some embodiments.

In some embodiments, display device 100 includes one or more components described herein with respect to FIG. 2. In some embodiments, display device 100 includes additional components not shown in FIG. 2.

FIG. 2 is a block diagram of system 200 in accordance with some embodiments. The system 200 shown in FIG. 2 includes display device 205 (which corresponds to display device 100 shown in FIG. 1), imaging device 235, and input interface 240 that are each coupled to console 210. While FIG. 2 shows an example of system 200 including display device 205, imaging device 235, and input interface 240, in other embodiments, any number of these components may be included in system 200. For example, there may be multiple display devices 205 each having associated input interface 240 and being monitored by one or more imaging devices 235, with each display device 205, input interface 240, and imaging devices 235 communicating with console 210. In alternative configurations, different and/or additional components may be included in system 200. For example, in some embodiments, console 210 is connected via a network (e.g., the Internet) to system 200 or is self-contained as part of display device 205 (e.g., physically located inside display device 205). In some embodiments, display device 205 is used to create mixed reality by adding in a view of the real surroundings. Thus, display device 205 and system 200 described here can deliver augmented reality, virtual reality, and mixed reality.

In some embodiments, as shown in FIG. 1, display device 205 corresponds to display device 100 and is a head-mounted display that presents media to a user. Examples of media presented by display device 205 include one or more images, video, audio, or some combination thereof. In some embodiments, audio is presented via an external device (e.g., speakers and/or headphones) that receives audio information from display device 205, console 210, or both, and presents audio data based on the audio information. In some embodiments, display device 205 immerses a user in an augmented environment.

In some embodiments, display device 205 also acts as an augmented reality (AR) headset. In these embodiments, display device 205 augments views of a physical, real-world environment with computer-generated elements (e.g., images, video, sound, etc.). Moreover, in some embodiments, display device 205 is able to cycle between different types of operation. Thus, display device 205 operate as a virtual reality (VR) device, an augmented reality (AR) device, as glasses or some combination thereof (e.g., glasses with no optical correction, glasses optically corrected for the user, sunglasses, or some combination thereof) based on instructions from application engine 255.

Display device 205 includes electronic display 215, one or more processors 216, eye tracking module 217, adjustment module 218, one or more locators 220, one or more position sensors 225, one or more position cameras 222, memory 228, inertial measurement unit (IMU) 230, one or more optical assemblies 260, or a subset or superset thereof (e.g., display device 205 with electronic display 215, optical assembly 260, without any other listed components). Some embodiments of display device 205 have different modules than those described here. Similarly, the functions can be distributed among the modules in a different manner than is described here.

One or more processors 216 (e.g., processing units or cores) execute instructions stored in memory 228. Memory 228 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 228, or alternately the non-volatile memory device(s) within memory 228, includes a non-transitory computer readable storage medium. In some embodiments, memory 228 or the computer readable storage medium of memory 228 stores programs, modules and data structures, and/or instructions for displaying one or more images on electronic display 215.

Electronic display 215 displays images to the user in accordance with data received from console 210 and/or processor(s) 216. In various embodiments, electronic display 215 may comprise a single adjustable display element or multiple adjustable display elements (e.g., a display for each eye of a user). In some embodiments, electronic display 215 is configured to project images to the user through one or more optical assemblies 260.

In some embodiments, the display element includes one or more light emission devices and a corresponding array of spatial light modulators. A spatial light modulator is an array of electro-optic pixels, opto-electronic pixels, some other array of devices that dynamically adjust the amount of light transmitted by each device, or some combination thereof. These pixels are placed behind one or more lenses. In some embodiments, the spatial light modulator is an array of liquid crystal based pixels in an LCD (a Liquid Crystal Display). Examples of the light emission devices include: an organic light emitting diode, an active-matrix organic light-emitting diode, a light emitting diode, some type of device capable of being placed in a flexible display, or some combination thereof. The light emission devices include devices that are capable of generating visible light (e.g., red, green, blue, etc.) used for image generation. The spatial light modulator is configured to selectively attenuate individual light emission devices, groups of light emission devices, or some combination thereof. Alternatively, when the light emission devices are configured to selectively attenuate individual emission devices and/or groups of light emission devices, the display element includes an array of such light emission devices without a separate emission intensity array.

One or more optical components in the one or more optical assemblies 260 direct light from the arrays of light emission devices (optionally through the emission intensity arrays) to locations within each eyebox and ultimately to the back of the user's retina(s). An eyebox is a region that is occupied by an eye of a user of display device 205 (e.g., a user wearing display device 205) who is viewing images from display device 205. In some cases, the eyebox is represented as a 10 mm×10 mm square. In some embodiments, the one or more optical components include one or more coatings, such as anti-reflective coatings, and one or more polarization volume holograms (PVH).

In some embodiments, the display element includes an infrared (IR) detector array that detects IR light that is retro-reflected from the retinas of a viewing user, from the surface of the corneas, lenses of the eyes, or some combination thereof. The IR detector array includes an IR sensor or a plurality of IR sensors that each correspond to a different position of a pupil of the viewing user's eye. In alternate embodiments, other eye tracking systems may also be employed.

Eye tracking module 217 determines locations of each pupil of a user's eyes. In some embodiments, eye tracking module 217 instructs electronic display 215 to illuminate the eyebox with IR light (e.g., via IR emission devices in the display element).

A portion of the emitted IR light will pass through the viewing user's pupil and be retro-reflected from the retina toward the IR detector array, which is used for determining the location of the pupil. Additionally or alternatively, the reflection off of the surfaces of the eye is used to also determine location of the pupil. In some cases, the IR detector array scans for retro-reflection and identifies which IR emission devices are active when retro-reflection is detected. Eye tracking module 217 may use a tracking lookup table and the identified IR emission devices to determine the pupil locations for each eye. The tracking lookup table maps the received signals on the IR detector array to locations (corresponding to pupil locations) in each eyebox. In some embodiments, the tracking lookup table is generated via a calibration procedure (e.g., user looks at various known reference points in an image and eye tracking module 217 maps the locations of the user's pupil while looking at the reference points to corresponding signals received on the IR tracking array). As mentioned above, in some embodiments, system 200 may use other eye tracking systems than the embedded IR eye tracking system described herein.

Adjustment module 218 generates an image frame based on the determined locations of the pupils. In some embodiments, this sends a discrete image to the display that will tile sub-images together thus a coherent stitched image will appear on the back of the retina. Adjustment module 218 adjusts an output (i.e. the generated image frame) of electronic display 215 based on the detected locations of the pupils. Adjustment module 218 instructs portions of electronic display 215 to pass image light to the determined locations of the pupils. In some embodiments, adjustment module 218 also instructs the electronic display not to provide image light to positions other than the determined locations of the pupils. Adjustment module 218 may, for example, block and/or stop light emission devices whose image light falls outside of the determined pupil locations, allow other light emission devices to emit image light that falls within the determined pupil locations, translate and/or rotate one or more display elements, dynamically adjust curvature and/or refractive power of one or more active lenses in the lens (e.g., microlens) arrays, or some combination thereof.

Optional locators 220 are objects located in specific positions on display device 205 relative to one another and relative to a specific reference point on display device 205. A locator 220 may be a light emitting diode (LED), a corner cube reflector, a reflective marker, a type of light source that contrasts with an environment in which display device 205 operates, or some combination thereof. In embodiments where locators 220 are active (i.e., an LED or other type of light emitting device), locators 220 may emit light in the visible band (e.g., about 400 nm to 750 nm), in the infrared band (e.g., about 750 nm to 1 mm), in the ultraviolet band (about 100 nm to 400 nm), some other portion of the electromagnetic spectrum, or some combination thereof.

In some embodiments, locators 220 are located beneath an outer surface of display device 205, which is transparent to the wavelengths of light emitted or reflected by locators 220 or is thin enough to not substantially attenuate the wavelengths of light emitted or reflected by locators 220. Additionally, in some embodiments, the outer surface or other portions of display device 205 are opaque in the visible band of wavelengths of light. Thus, locators 220 may emit light in the IR band under an outer surface that is transparent in the IR band but opaque in the visible band.

IMU 230 is an electronic device that generates calibration data based on measurement signals received from one or more position sensors 225. Position sensor 225 generates one or more measurement signals in response to motion of display device 205. Examples of position sensors 225 include: one or more accelerometers, one or more gyroscopes, one or more magnetometers, another suitable type of sensor that detects motion, a type of sensor used for error correction of IMU 230, or some combination thereof. Position sensors 225 may be located external to IMU 230, internal to IMU 230, or some combination thereof.

Based on the one or more measurement signals from one or more position sensors 225, IMU 230 generates first calibration data indicating an estimated position of display device 205 relative to an initial position of display device 205. For example, position sensors 225 include multiple accelerometers to measure translational motion (forward/back, up/down, left/right) and multiple gyroscopes to measure rotational motion (e.g., pitch, yaw, roll). In some embodiments, IMU 230 rapidly samples the measurement signals and calculates the estimated position of display device 205 from the sampled data. For example, IMU 230 integrates the measurement signals received from the accelerometers over time to estimate a velocity vector and integrates the velocity vector over time to determine an estimated position of a reference point on display device 205. Alternatively, IMU 230 provides the sampled measurement signals to console 210, which determines the first calibration data. The reference point is a point that may be used to describe the position of display device 205. While the reference point may generally be defined as a point in space; however, in practice the reference point is defined as a point within display device 205 (e.g., a center of IMU 230).

In some embodiments, IMU 230 receives one or more calibration parameters from console 210. As further discussed below, the one or more calibration parameters are used to maintain tracking of display device 205. Based on a received calibration parameter, IMU 230 may adjust one or more IMU parameters (e.g., sample rate). In some embodiments, certain calibration parameters cause IMU 230 to update an initial position of the reference point so it corresponds to a next calibrated position of the reference point. Updating the initial position of the reference point as the next calibrated position of the reference point helps reduce accumulated error associated with the determined estimated position. The accumulated error, also referred to as drift error, causes the estimated position of the reference point to "drift" away from the actual position of the reference point over time.

Imaging device 235 generates calibration data in accordance with calibration parameters received from console 210. Calibration data includes one or more images showing observed positions of locators 220 that are detectable by imaging device 235. In some embodiments, imaging device 235 includes one or more still cameras, one or more video cameras, any other device capable of capturing images including one or more locators 220, or some combination thereof. Additionally, imaging device 235 may include one or more filters (e.g., used to increase signal to noise ratio). Imaging device 235 is configured to optionally detect light emitted or reflected from locators 220 in a field of view of imaging device 235. In embodiments where locators 220 include passive elements (e.g., a retroreflector), imaging device 235 may include a light source that illuminates some or all of locators 220, which retro-reflect the light toward the light source in imaging device 235. Second calibration data is communicated from imaging device 235 to console 210, and imaging device 235 receives one or more calibration parameters from console 210 to adjust one or more imaging parameters (e.g., focal length, focus, frame rate, ISO, sensor temperature, shutter speed, aperture, etc.).

In some embodiments, display device 205 includes one or more optical assemblies 260. In some embodiments, display device 205 optionally includes a single optical assembly 260 or multiple optical assemblies 260 (e.g., an optical assembly 260 for each eye of a user). In some embodiments, the one or more optical assemblies 260 receive image light for the computer generated images from the electronic display device(s) 215 and direct the image light toward an eye or eyes of a user. The computer-generated images include still images, animated images, and/or a combination thereof. The computer-generated images include objects that appear to be two-dimensional and/or three-dimensional objects.

In some embodiments, electronic display device 215 projects computer-generated images to one or more reflective elements (not shown), and the one or more optical assemblies receive the image light from the one or more reflective elements and direct the image light to the eye(s) of the user. In some embodiments, the one or more reflective elements are partially transparent (e.g., the one or more reflective elements have a transmittance of at least 15%, 20%, 25%, 30%, 35%, 40%, 45%, or 50%), which allows transmission of ambient light. In such embodiments, computer-generated images projected by electronic display 215 are superimposed with the transmitted ambient light (e.g., transmitted ambient image) to provide augmented reality images.

Input interface 240 is a device that allows a user to send action requests to console 210. An action request is a request to perform a particular action. For example, an action request may be to start or end an application or to perform a particular action within the application. Input interface 240 may include one or more input devices. Example input devices include: a keyboard, a mouse, a game controller, data from brain signals, data from other parts of the human body, or any other suitable device for receiving action requests and communicating the received action requests to console 210. An action request received by input interface 240 is communicated to console 210, which performs an action corresponding to the action request. In some embodiments, input interface 240 may provide haptic feedback to the user in accordance with instructions received from console 210. For example, haptic feedback is provided when an action request is received, or console 210 communicates instructions to input interface 240 causing input interface 240 to generate haptic feedback when console 210 performs an action.

Console 210 provides media to display device 205 for presentation to the user in accordance with information received from one or more of: imaging device 235, display device 205, and input interface 240. In the example shown in FIG. 2, console 210 includes application store 245, tracking module 250, and application engine 255. Some embodiments of console 210 have different modules than those described in conjunction with FIG. 2. Similarly, the functions further described herein may be distributed among components of console 210 in a different manner than is described here.

When application store 245 is included in console 210, application store 245 stores one or more applications for execution by console 210. An application is a group of instructions, that when executed by a processor, is used for generating content for presentation to the user. Content generated by the processor based on an application may be in response to inputs received from the user via movement of display device 205 or input interface 240. Examples of applications include: gaming applications, conferencing applications, video playback application, or other suitable applications.

When tracking module 250 is included in console 210, tracking module 250 calibrates system 200 using one or more calibration parameters and may adjust one or more calibration parameters to reduce error in determination of the position of display device 205. For example, tracking module 250 adjusts the focus of imaging device 235 to obtain a more accurate position for observed locators on display device 205. Moreover, calibration performed by tracking module 250 also accounts for information received from IMU 230. Additionally, if tracking of display device 205 is lost (e.g., imaging device 235 loses line of sight of at least a threshold number of locators 220), tracking module 250 re-calibrates some or all of system 200.

In some embodiments, tracking module 250 tracks movements of display device 205 using second calibration data from imaging device 235. For example, tracking module 250 determines positions of a reference point of display device 205 using observed locators from the second calibration data and a model of display device 205. In some embodiments, tracking module 250 also determines positions of a reference point of display device 205 using position information from the first calibration data. Additionally, in some embodiments, tracking module 250 may use portions of the first calibration data, the second calibration data, or some combination thereof, to predict a future location of display device 205. Tracking module 250 provides the estimated or predicted future position of display device 205 to application engine 255.

Application engine 255 executes applications within system 200 and receives position information, acceleration information, velocity information, predicted future positions, or some combination thereof of display device 205 from tracking module 250. Based on the received information, application engine 255 determines content to provide to display device 205 for presentation to the user. For example, if the received information indicates that the user has looked to the left, application engine 255 generates content for display device 205 that mirrors the user's movement in an augmented environment. Additionally, application engine 255 performs an action within an application executing on console 210 in response to an action request received from input interface 240 and provides feedback to the user that the action was performed. The provided feedback may be visual or audible feedback via display device 205 or haptic feedback via input interface 240.

Figure 3A:
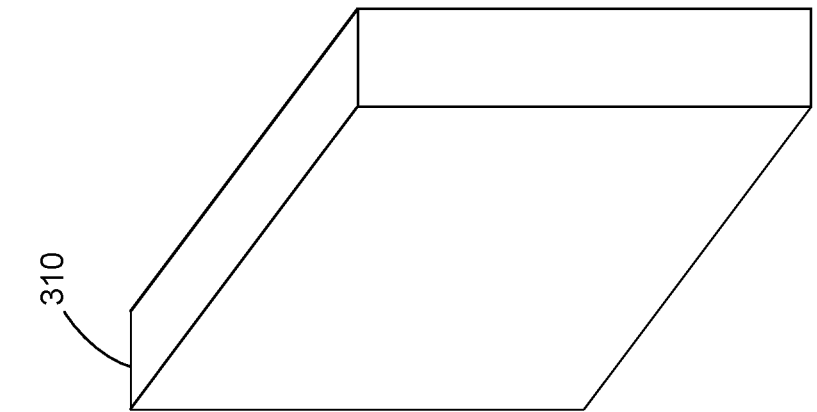
FIG. 3A is an isometric view of a display device in accordance with some embodiments.
Figure 3A:
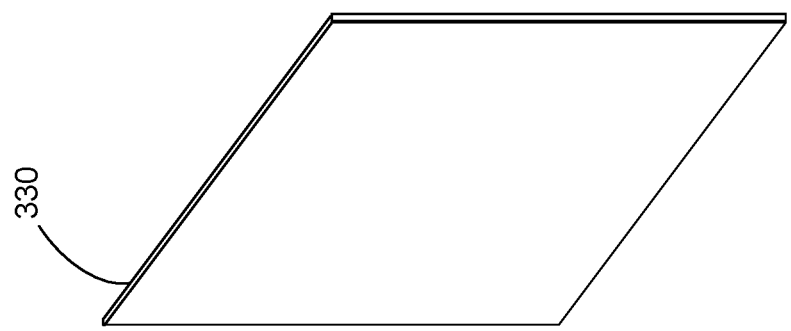
Figure 3A:
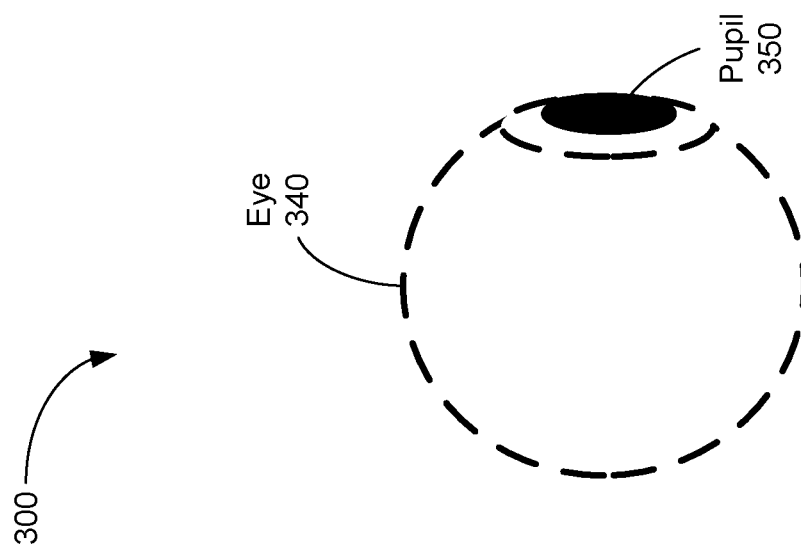

FIG. 3A is an isometric view of display device 300 in accordance with some embodiments. In some other embodiments, display device 300 is part of some other electronic display (e.g., a digital microscope, a head-mounted display device, etc.). In some embodiments, display device 300 includes light emission device 310 and an optical assembly 330, which may include one or more lenses and/or other optical components. In some embodiments, display device 300 also includes an IR detector array.

Light emission device 310 emits image light and optional IR light toward the viewing user. Light emission device 310 includes one or more light emission components that emit light in the visible light (and optionally includes components that emit light in the IR). Light emission device 310 may include, e.g., an array of LEDs, an array of microLEDs, an array of OLEDs, or some combination thereof.

In some embodiments, light emission device 310 includes an emission intensity array (e.g., a spatial light modulator) configured to selectively attenuate light emitted from light emission device 310. In some embodiments, the emission intensity array is composed of a plurality of liquid crystal cells or pixels, groups of light emission devices, or some combination thereof. Each of the liquid crystal cells is, or in some embodiments, groups of liquid crystal cells are, addressable to have specific levels of attenuation. For example, at a given time, some of the liquid crystal cells may be set to no attenuation, while other liquid crystal cells may be set to maximum attenuation. In this manner, the emission intensity array is able to provide image light and/or control what portion of the image light is passed to the optical assembly 330. In some embodiments, display device 300 uses the emission intensity array to facilitate providing image light to a location of pupil 350 of eye 340 of a user, and minimize the amount of image light provided to other areas in the eyebox.

The optical assembly 330 includes one or more lenses. The one or more lenses in optical assembly 330 receive modified image light (e.g., attenuated light) from light emission device 310, and direct the modified image light to a location of pupil 350. The optical assembly 330 may include additional optical components, such as color filters, mirrors, etc.

An optional IR detector array detects IR light that has been retro-reflected from the retina of eye 340, a cornea of eye 340, a crystalline lens of eye 340, or some combination thereof. The IR detector array includes either a single IR sensor or a plurality of IR sensitive detectors (e.g., photodiodes). In some embodiments, the IR detector array is separate from light emission device 310. In some embodiments, the IR detector array is integrated into light emission device 310.

In some embodiments, light emission device 310 including an emission intensity array make up a display element. Alternatively, the display element includes light emission device 310 (e.g., when light emission device 310 includes individually adjustable pixels) without the emission intensity array. In some embodiments, the display element additionally includes the IR array. In some embodiments, in response to a determined location of pupil 350, the display element adjusts the emitted image light such that the light output by the display element is refracted by one or more lenses toward the determined location of pupil 350, and not toward other locations in the eyebox.

In some embodiments, display device 300 includes one or more broadband sources (e.g., one or more white LEDs) coupled with a plurality of color filters, in addition to, or instead of, light emission device 310.

Figure 3B:
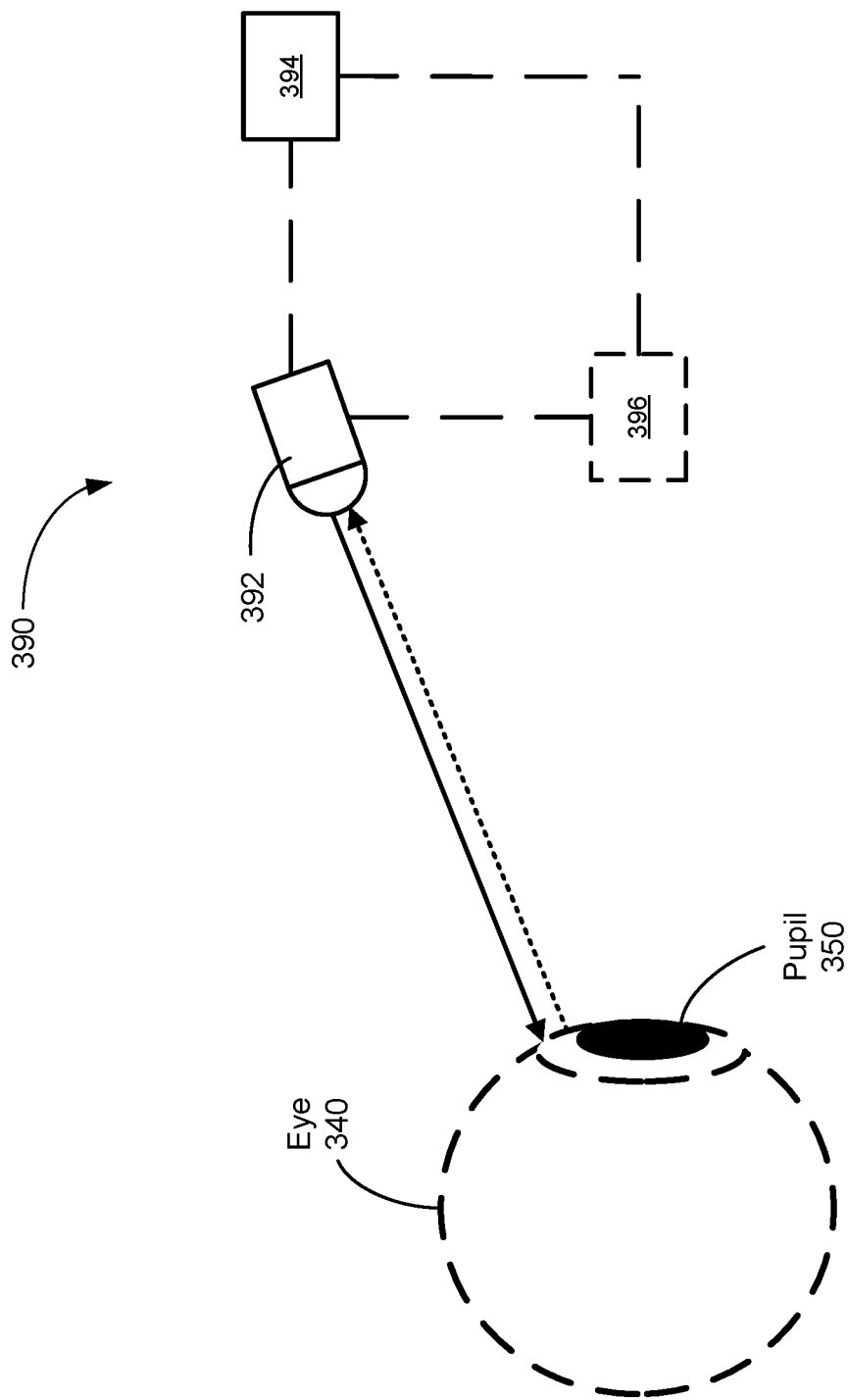
FIG. 3B is a schematic diagram illustrating an eye-tracking device including an optical device accordance with some embodiments.

FIG. 3B illustrates an eye-tracking device 390 that uses self-mixing interferometry to determine movement information regarding the eye 340 (e.g., movement information regarding the pupil 350 of the eye 340). Eye-tracking device 390 includes one or more optical devices 392 and one or more processors 394 coupled to (e.g., in communication with) the one or more optical devices 392. The one or more optical devices 392 are configured to perform interferometric measurements, generate one or more signals based on the interferometric measurements, and transmit the one or more signals to the one or more processors 394. The one or more processors 394 are configured to determine movement information of the eye 340 (e.g., movement information of the pupil based on the one or more signals received from the optical device 392.

In some embodiments, the eye-tracking device 390 also includes an electrical source 396 that is coupled to the optical device 392 (e.g., coupled to a light source of the optical device) and configured to control operation of a light source in the optical device. For example, the electrical source 396 may be configured to change a power or intensity of light output from the optical device 392. In some embodiments, the electrical source 396 is coupled to the one or more processors 394 so that the one or more processors 394 control operations of the electrical source 396 (e.g., the one or more processors 394 control the electrical output provided to the optical device 392, which, in turn, changes the power or intensity of light output from the optical device 392).

In some embodiments, eye-tracking device 390 (e.g., eye-tracker) may include one or more additional optical components. FIGS. 10-13B illustrate examples of additional optical components that may be included as part of the eye-tracking device 390.

FIGS. 4A-4C, 5A, 5B, and 6A-6C illustrate example optical devices corresponding to optical device 392. FIGS. 7B and 9C illustrate examples of different configurations of optical devices in eye-tracking device 390 when the eye-tracking device 390 includes a plurality of optical devices 392 or a plurality of light sources.

Figure 4A:
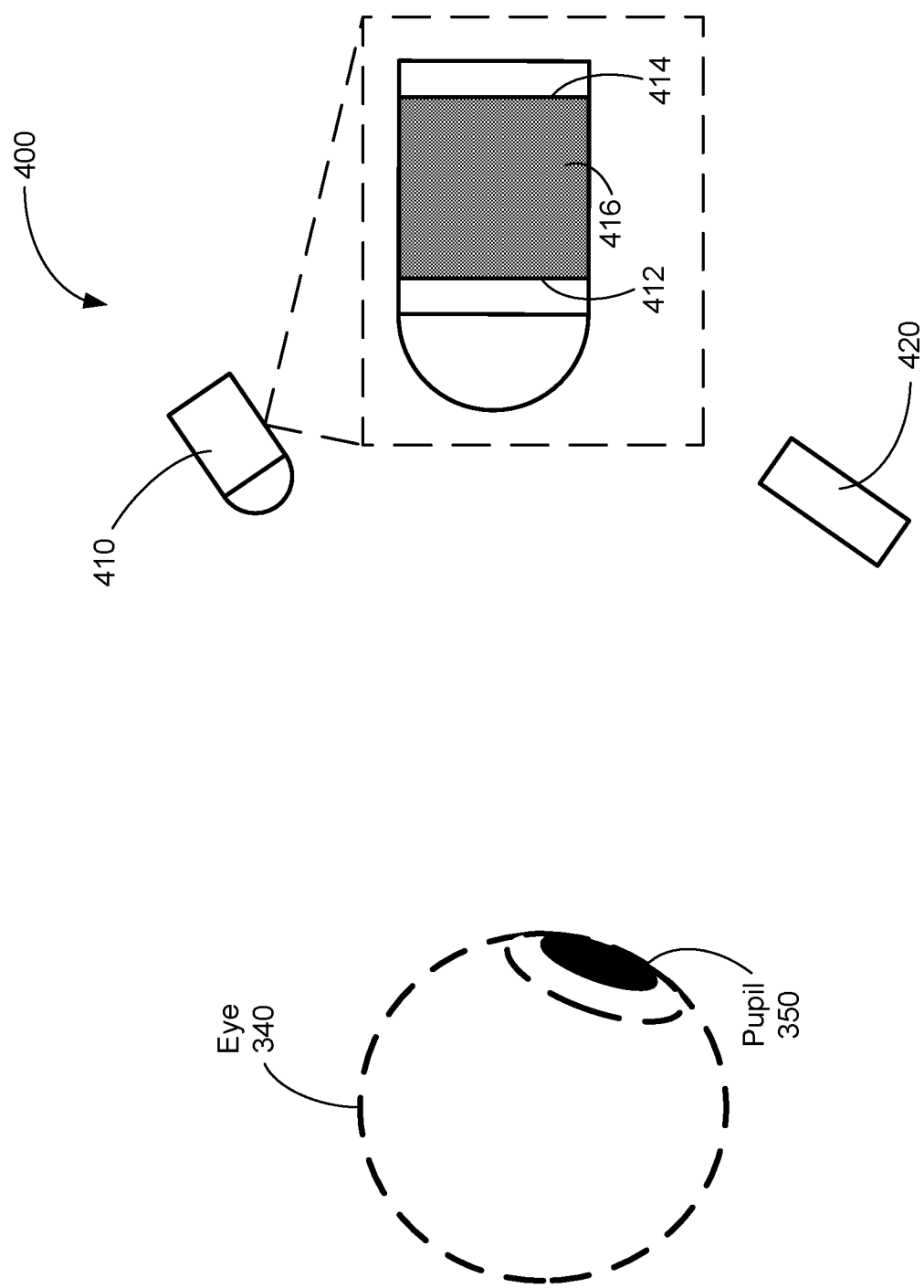
FIGS. 4A-4C are schematic diagrams illustrating an optical device with an external sensor in accordance with some embodiments.
Figure 4B:
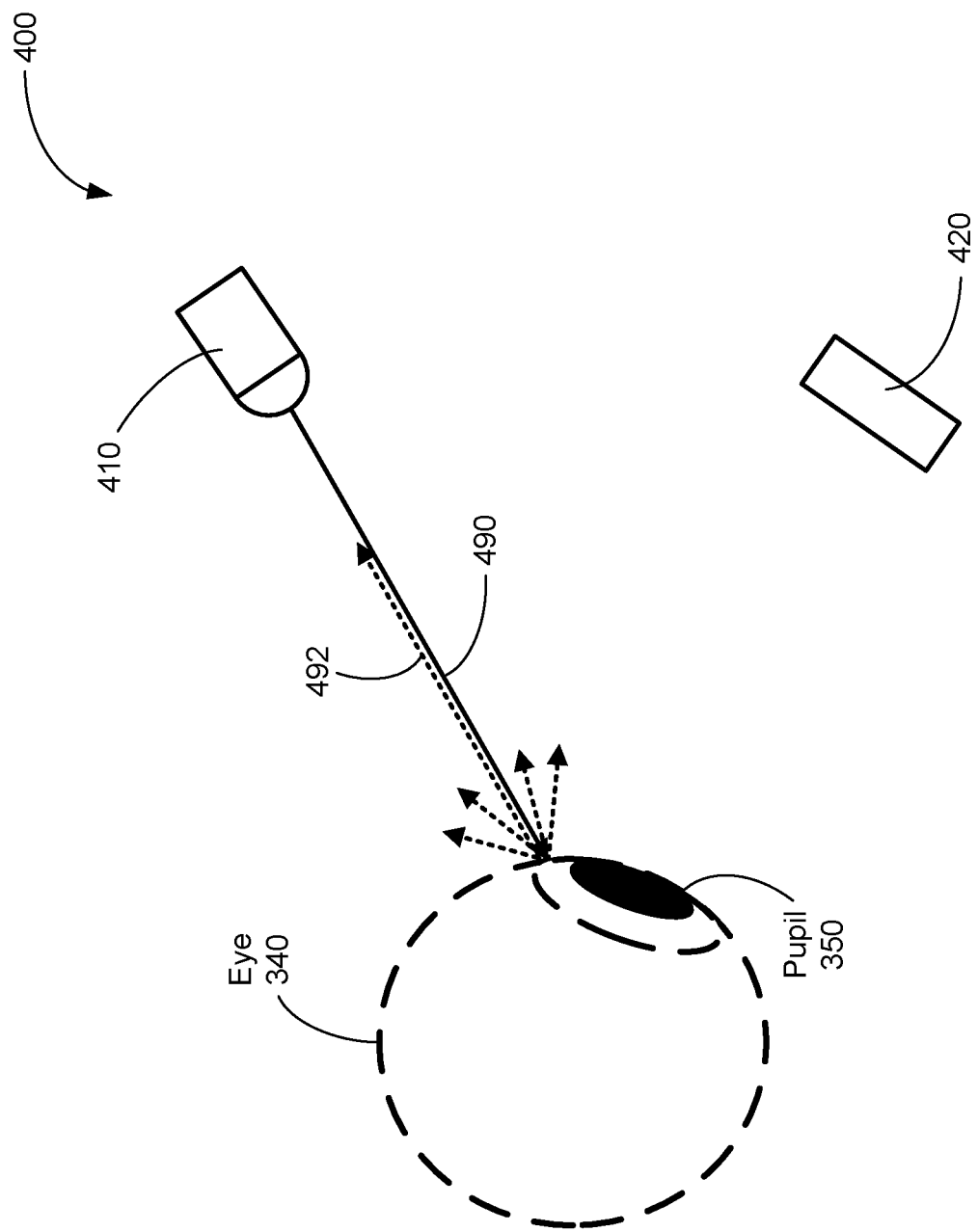
Figure 4C:
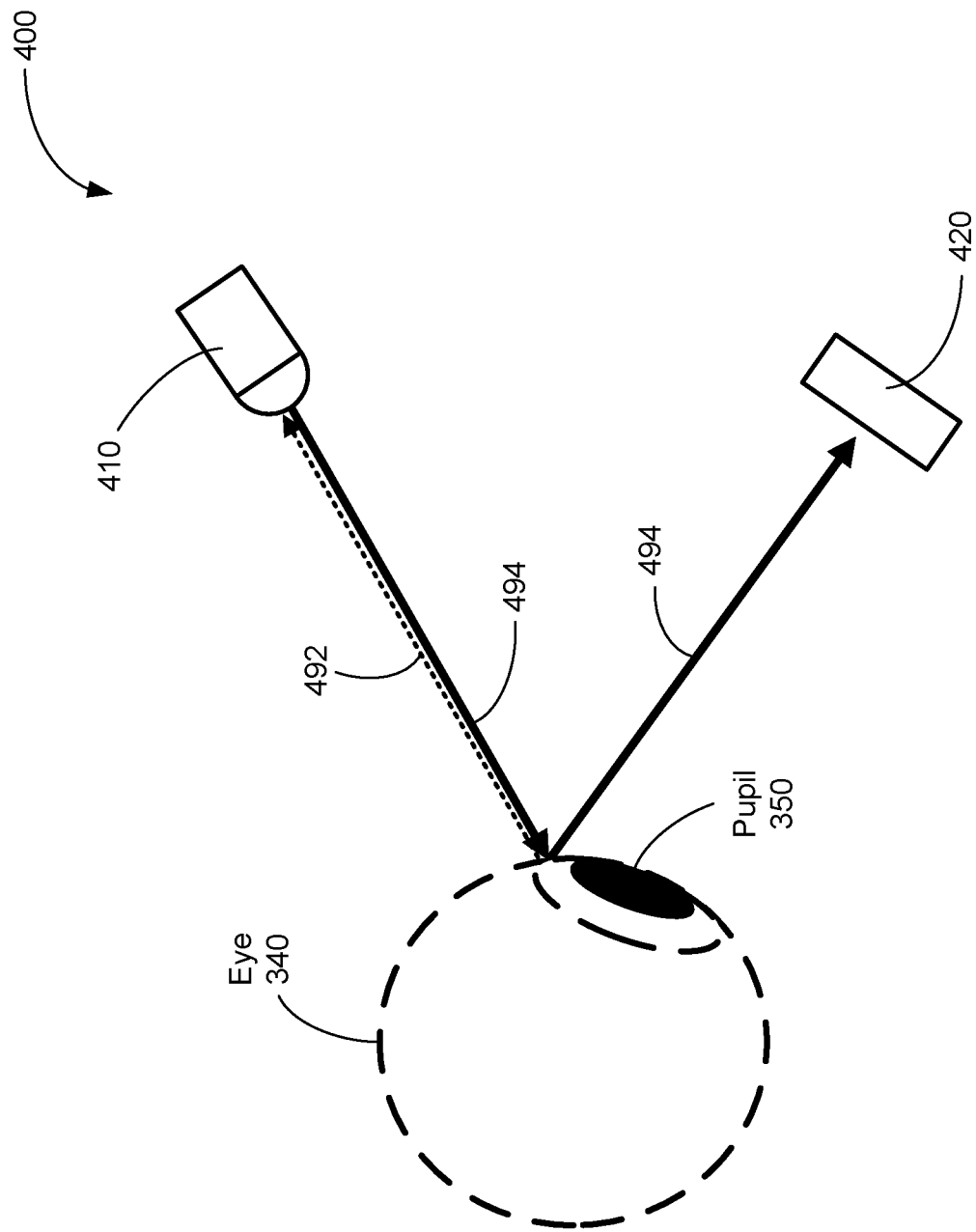

FIGS. 4A-4C are schematic diagrams illustrating an optical device 400, corresponding to optical device 392, that includes an external light sensor 420 in accordance with some embodiments. As shown in FIG. 4A, optical device 400 includes a light source 410 (e.g., laser source) and a light sensor 420 (e.g., photodetector). In FIGS. 4A-4C, the light sensor 420 is positioned separately from the light source 410.

The light source 410 includes a cavity 416 (e.g., an optical cavity, which may be a laser cavity) defined by two reflective elements (e.g., reflective surfaces 412 and 414). In some embodiments, the reflective elements are distributed Bragg reflectors.

In some embodiments, the light source 410 may be a laser source, such as a vertical cavity surface emitting laser (VCSEL) or a vertical external cavity surface emitting laser (VECSEL).

The cavity 416 is used to generate coherent light and light source 410 is positioned to output at least a portion of the coherent light towards an eye 340 of a user. The surface 412 is semi-reflective (e.g., the surface 412 is a partially reflective and partially transmissive mirror). For example, the reflectance of the surface 414 is greater than the reflectance of the surface 412 (e.g., the surface 414 has a reflectance of 100%, 99.99%, 99.9%, 99%, 98%, 97%, 96%, 95%, 90% or an interval between any two of the aforementioned values, and the surface 412 has a reflectance of 99.99%, 99.9%, 99%, 98%, 97%, 96%, 95%, 90% or an interval between any two of the aforementioned values). In some configurations, the surface 412 has a transmittance of at least 0.01%, 0.1%, 1%, or an interval between any two of the aforementioned values. The surface 412 reflects a portion of the light propagating toward the surface 412 within the cavity 416 back toward the surface 414 and transmit a portion of the light propagating toward the surface 412 within the cavity 416 (e.g., the surface 412 is configured to reflect at least a portion of the light generated inside the cavity 416 back into the cavity 416 and to transmit at least a portion of the light generated inside the cavity 416). As shown in FIG. 4B, the transmitted light is emitted from the light source 410 as coherent light 490. The light source 410 is also configured to (e.g., positioned to) receive at least a portion of the coherent light back from the eye 340 of the user as feedback light 492. The feedback light 492 enters the cavity 416 of the light source 410 and interferes with the generation of the coherent light inside the cavity 416, leading to a modulation of the intensity of the generated coherent light.

Referring to FIG. 4C, the modulated coherent light 494 (e.g., coherent light with modulated intensity) is output from the light source 410 (e.g., output from cavity 416) and at least a portion of the modulated coherent light 494 is received and detected by the light sensor 420. The light sensor 420 is configured to generate one or more signals based on the detected intensity (e.g., modulated intensity) of the modulated coherent light 494. Information regarding movement information of the eye 340 (e.g., movement of the pupil 350 of the eye 340) can be determined by analyzing the modulated coherent light 494 or the one or more signals generated based on the modulated coherent light 494.

This measurement technique is known as "self-mixing interferometry," where coherent light (e.g., a laser beam) is reflected from a target (e.g., a target object such as an eye) back into the light source (e.g., the laser cavity) and the reflected light interferes with, and modulates, the coherent light generated inside the light source (e.g., modulates the power and/or intensity of the light generated by the light source). Position and/or movement information regarding the target can be determined from (e.g., based on, using) intensity or power measurements of the modulated coherent light. The self-mixing interferometry is also called "feedback interferometry," "induced-modulation interferometry," and "backscatter modulation interferometry."

In some embodiments, instead of a sensor located separately from a light source (e.g., the sensor 420 located separately from the light source 410), a sensor integrated with a light source is used.

Figure 5A:
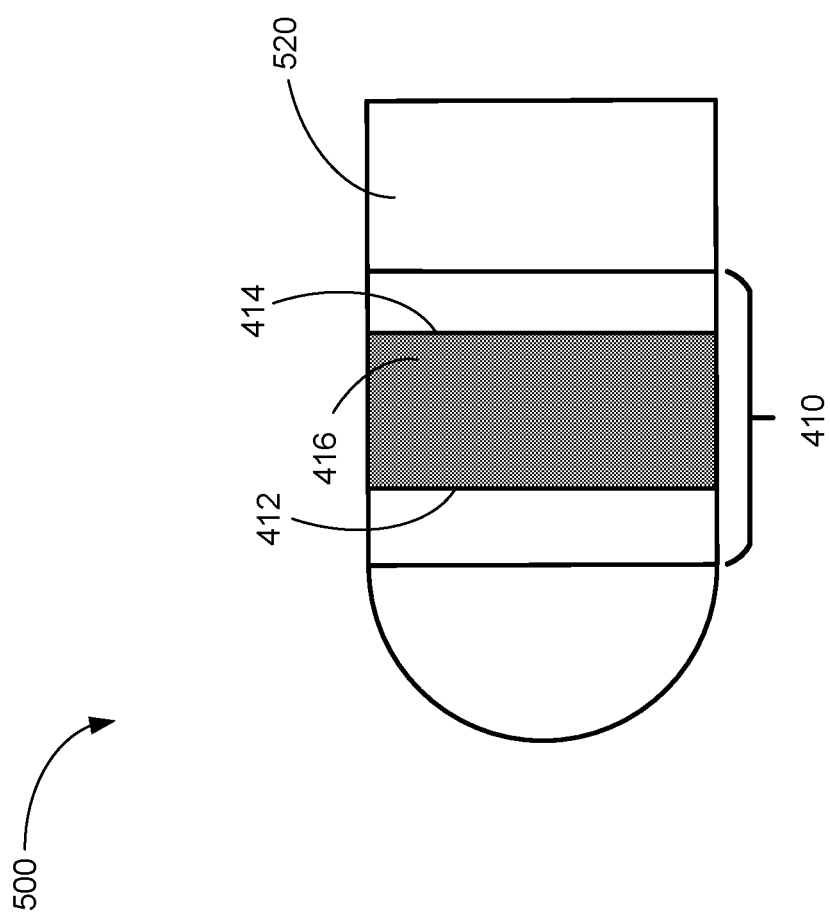
FIGS. 5A and 5B are schematic diagrams illustrating a vertically integrated optical device in accordance with some embodiments.
Figure 5B:
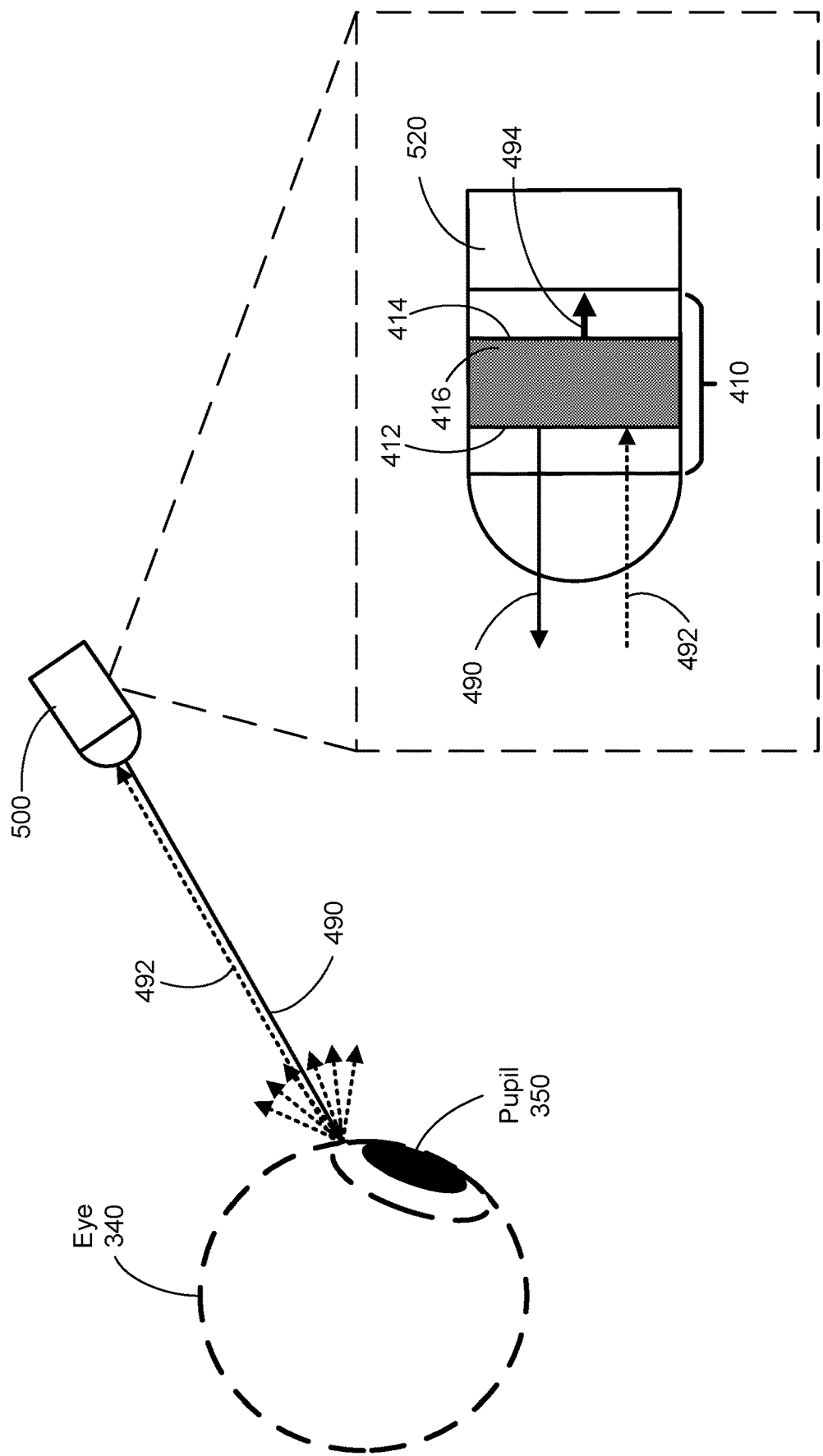

FIGS. 5A and 5B are schematic diagrams illustrating a vertically integrated optical device 500 in accordance with some embodiments. The optical device 500 is sometimes called an interferometer sensor. As shown in FIG. 5A, the optical device 500 includes a light source 410 and a vertically integrated light sensor 520 (e.g., photodetector) that is optically coupled to and vertically integrated with the light source 410. The light source 410 includes surfaces 412 and 414 that define a cavity 416. In FIG. 5A, both surfaces 412 and 414 are semi-reflective surfaces (e.g., partially reflective and partially transmissive mirrors) that are configured to reflect at least a portion of the coherent light generated inside the cavity 416 back into the cavity 416 and to transmit at least a portion of the light generated inside the cavity 416. For example, the surface 414 transmits a portion of the coherent light generated inside the cavity 416 toward the light sensor 520 so that the light sensor 520 may detect an intensity of the transmitted light.

The optical device 500 may be used in place of the optical device 392 shown in FIG. 3B. Referring to FIG. 5B, the optical device 500 (and hence, the light source 410 of the optical device 500) is configured to (e.g., positioned to) output coherent light 490, via the surface 412, towards the eye 340 of the user. The optical device 500 (and hence, the light source 410 of the optical device 500) is also configured to (e.g., positioned to) receive, via the surface 412, at least a portion of the coherent light back from the eye 340 of the user as feedback light 492. Since the surface 414 is semi-reflective (e.g., a partially reflective and partially transmissive mirror), at least a portion of the coherent light generated inside the cavity 416 is output from the light source 410, via the surface 414, toward the vertically integrated light sensor 520. The light sensor 520 is configured to (e.g., positioned to) receive (e.g., detect) at least a portion of the modulated coherent light 494 output from the light source 410 via the surface 414, and generate one or more signals based on the detected intensity (e.g., modulated intensity) of the modulated coherent light 494.

Figure 6A:
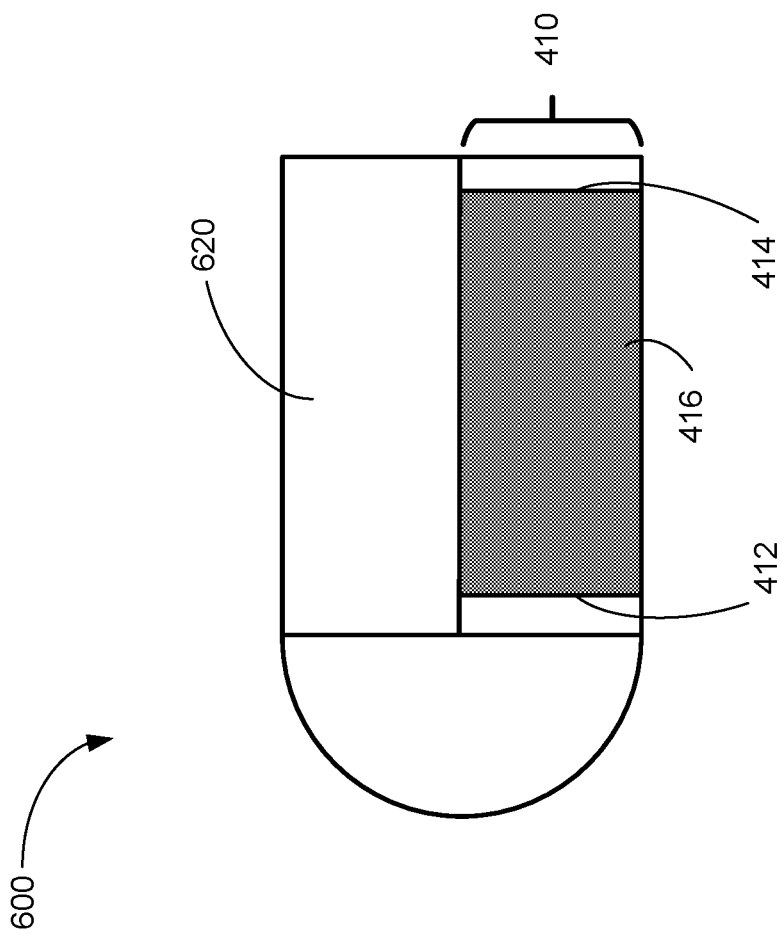
Figure 6B:
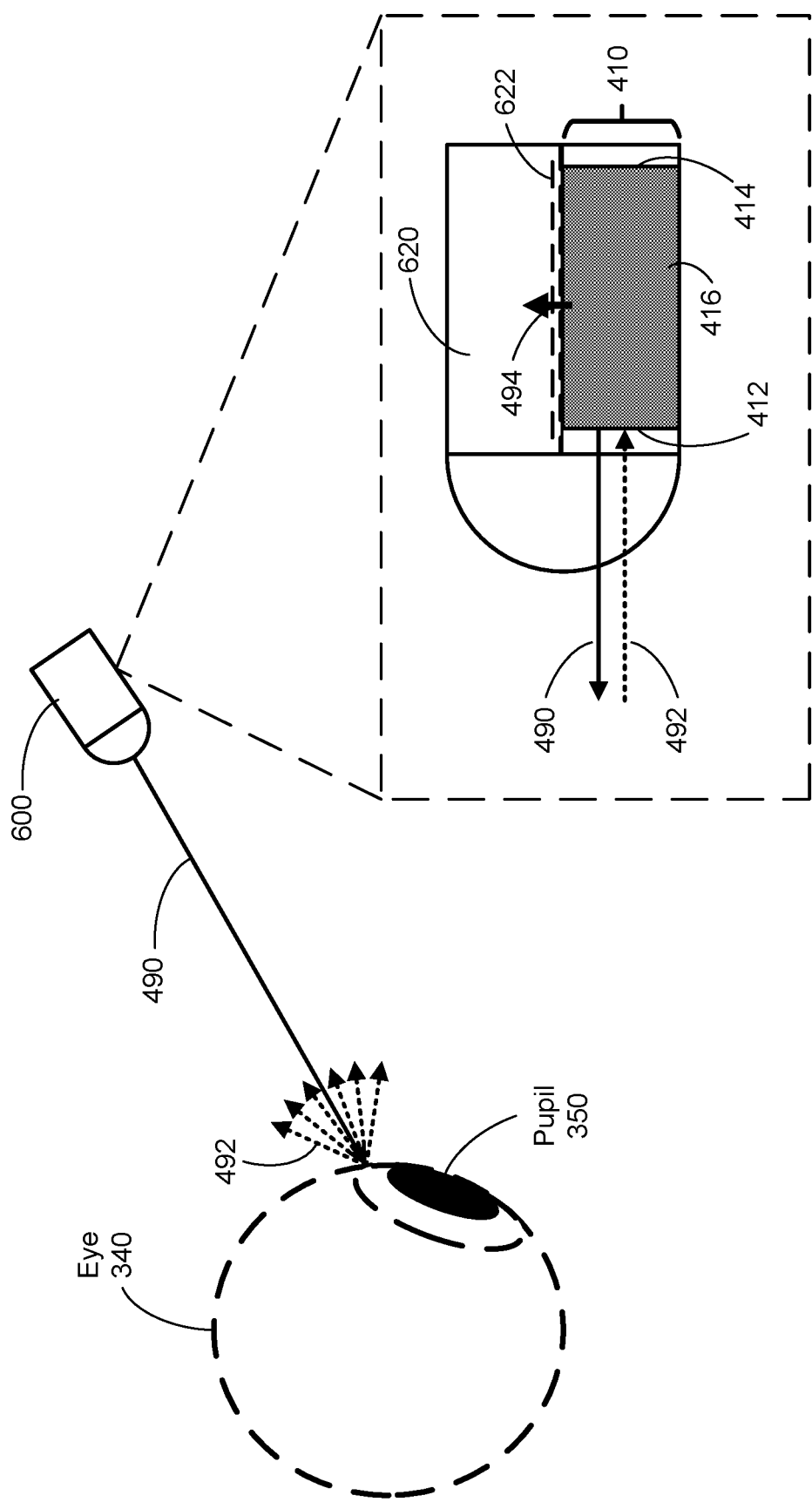

FIGS. 6A-6C are schematic diagrams illustrating a horizontally integrated optical device 600 in accordance with some embodiments. The optical device 600 is an interferometer sensor that includes a light source 410 (e.g., a laser source) configured to output coherent light 490 (e.g., laser light) and a light sensor 620 that is horizontally integrated with light source 410. The light source 410 includes surfaces 412 and 414 that define the cavity 416. Details regarding light source 410 are provided above with respect to FIGS. 4A-4C, 5A, and 5B. and thus, are not repeated herein.

The optical device 600 may be used in place of the optical device 392 shown in FIG. 3B. Referring to FIG. 6B, the light source 410 is configured to (e.g., positioned to) output coherent light 490, via the surface 412, towards the eye 340 of the user. The light source 410 is also configured to (e.g., positioned to) receive, via the surface 412, at least a portion of the coherent light back from the eye 340 of the user as feedback light 492 (e.g., the portion of the coherent light is scattered or reflected back from the eye 340 of the user). The feedback light 492 enters the cavity 416 of the light source 410 via the surface 412 and interferes with the coherent light generated inside the cavity 416, leading to a modulation of the intensity of the coherent light generated inside the cavity 416. A portion of the modulated light 494 leaks out of the cavity 416 and is detected by the light sensor 620. In some embodiments, a filter 622 (e.g., a neutral density filter or an aperture) is positioned between the cavity 416 and the light sensor 620 to attenuate (e.g., reduce intensity of) light transmitted from the cavity 416 to the light sensor 620.

Alternatively, the light sensor 620 detects the modulated light after the modulated light has been reflected by an external object (e.g., the target object, such as an eye). In FIG. 6C, the modulated coherent light 494 (e.g., coherent light with modulated intensity) is output from the light source 410 (e.g., output from the cavity 416) via the surface 412, and at least a portion of the modulated coherent light 494 is redirected back toward the light sensor 620 of the optical device 600 by a target object (e.g., the eye 340), and subsequently received and detected by the light sensor 620. In some embodiments, a barrier 624 is positioned between the cavity 416 and the light sensor 620 to block transmission of light from the cavity 416 to the light sensor 620. The horizontally integrated light sensor 620 is configured to generate one or more signals based on the detected intensity (e.g., modulated intensity) of the modulated coherent light 494. Information regarding movement information of the eye 340 (e.g., movement of the pupil 350 of the eye 340) can be determined by analyzing the modulated coherent light 494 or the one or more signals generated based on the modulated coherent light 494.

Figure 7A:
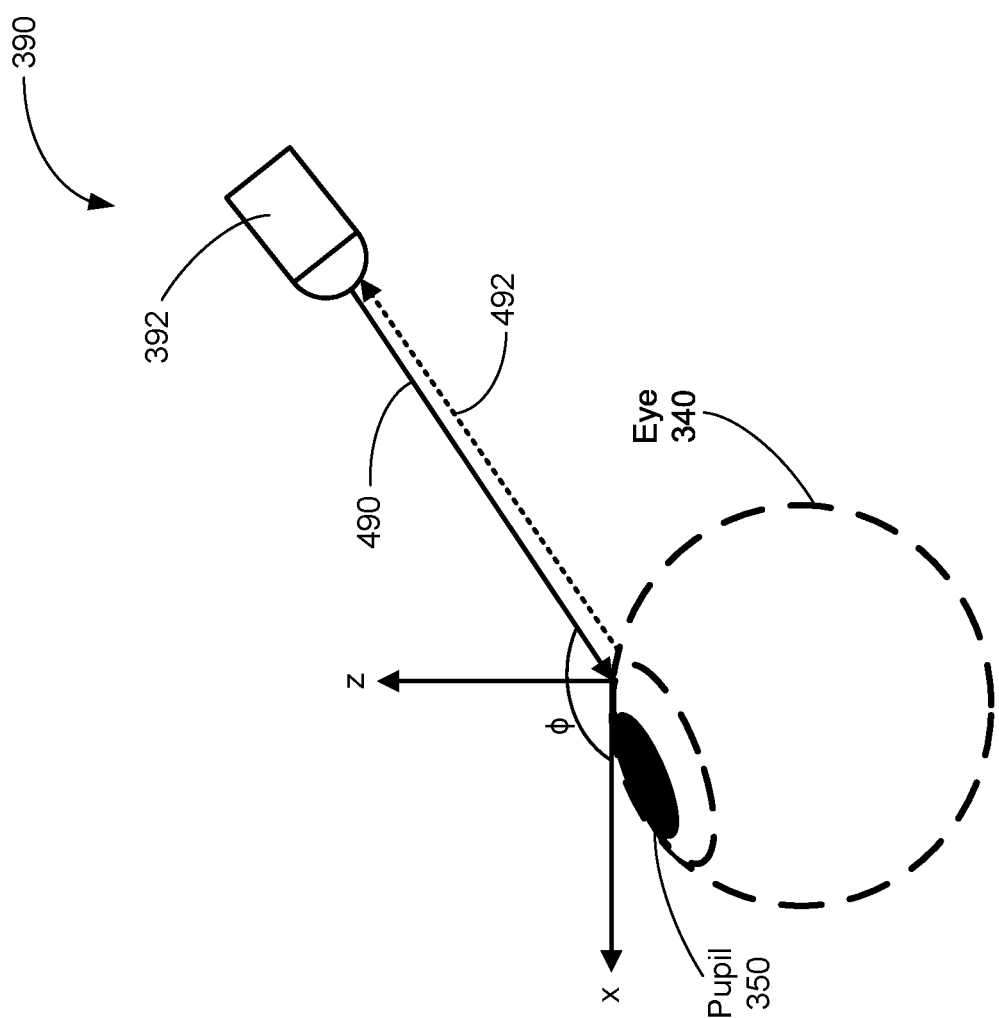
FIG. 7A is a schematic diagram illustrating tracking eye movement using an optical device in accordance with some embodiments.
Figure 7B:
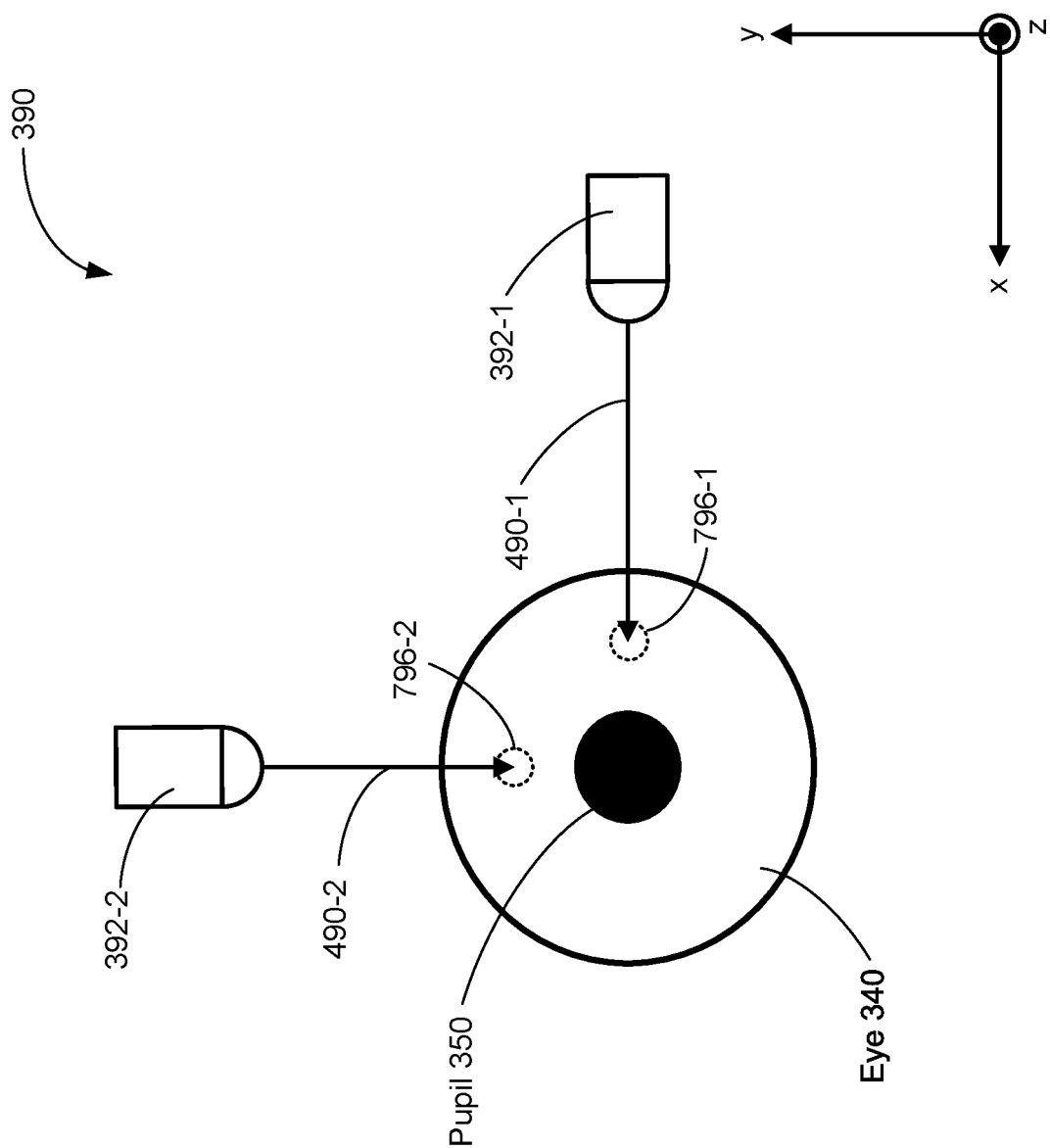
FIG. 7B is a schematic diagram illustrating an eye-tracking device that includes a plurality of optical devices in accordance with some embodiments.

FIG. 7A is a schematic diagram illustrating tracking eye movement using an eye-tracking device 390 in accordance with some embodiments. At least a portion of the coherent light 490 output from the optical device 392 is back-reflected or back-scattered from the eye 340 and received at the optical device 392 as feedback light 492. The feedback light 492 modulates an intensity of the coherent light 490 in the optical device 392. Information regarding position and movement of the eye 340 can be determined from (e.g., based on, using) intensity measurements of the modulated coherent light (e.g., modulated coherent light 494, described above with respect to FIGS. 4A-4C, 5A and 5B, and 6A-6C).

In FIG. 7A, the coherent light 490 output from the optical device 392 (which may have a structure analogous to that of optical device 400, 500, or 600) is incident on a surface of an eye 340 at an angle $\phi$ in the x-z plane. Thus, measurements received at the optical device 392 are sensitive to a movement of the eye 340 (or pupil 350 of the eye 340) in the direction of light 490. A movement of the surface (e.g., a surface of the eye 340) in the x-direction has a component in the direction of light 490 (e.g., x×sin $\phi$). When the eye 340 (or the pupil 350 of the eye 340) is stationary in the direction of light 490 (e.g., the surface of the eye 340 does not have movement in the direction of light 490), the mixing of feedback light 492 with the coherent light 490 will result in a uniform undulation of the coherent light 490 in time (characterized by a frequency $f_D$).

When the eye 340 (or a portion of the eye 340) moves in a direction non-perpendicular to the direction of light 490, the movement will cause a Doppler shift in the feedback light 492 (e.g., the frequency of feedback light 492 shifts relative to the frequency of the coherent light 490). The Doppler shift is proportional to the velocity of the eye 340 (or a portion thereof) along the direction of light 490, which can be described as follows:

$$f_V = 2v \times \cos \phi / \lambda$$

where $f_V$ is the Doppler shift, v is the velocity of the eye, $\phi$ is an angle between the direction of the movement and the direction of light 490, and $\lambda$ is the wavelength of light 490.

When the target object moves away from the optical device 392, the frequency of the feedback light 492 is $f_D+f_V$, and when the target object moves closer to the optical device 392, the frequency of the feedback light 492 is $f_D-f_V$.

Interference of the Doppler-shifted feedback light 492 with the coherent light 490 will result in a different modulation pattern compared to interference of non-Doppler-shifted feedback light 492 with the coherent light 490. Thus, movement of the eye 340 can be determined from intensity measurements of the modulated coherent light 494.

FIG. 7B is a schematic diagram illustrating eye-tracking device 390 (e.g., eye-tracker) that includes a plurality of optical devices 392 in accordance with some embodiments. The eye-tracking device 390 includes a plurality of (e.g., two or more) optical devices 392, each of which may correspond to any of the optical devices 400, 500, and 600. In 7B, two optical devices 392-1 and 392-2 are shown. Optical device 392-1 is positioned so that coherent light 490-1 output from a light source of the optical device 392-1 is incident upon the eye 340 in the x-z plane (as shown in FIG. 7A). In contrast, optical device 392-2 is positioned so that coherent light 490-2 output from a light source of the optical device 392-2 is incident upon the eye 340 in the y-z plane. Thus, the eye-tracking device 390 is sensitive to a position and movement of the eye 340 in both the x- and y-directions. By employing two optical devices 392-1 and 392-2, the eye-tracking device 390 is able to determine eye position and eye movement information in two dimensions (e.g., in the x-direction and the y-direction). For example, the coherent light 490-1 is output by a light source of the optical device 392-1. The modulated coherent light generated from the interference of feedback light with coherent light 490-1 is received by a light sensor of the optical device 392-1. The light sensor of the optical device 392-1 generates one or more signals based on the received (e.g., detected) modulated coherent light. Information regarding eye movement (e.g., movement of a portion 796-1 of the eye 340) along the x-direction can be determined using the one or more signals generated by the light sensor of optical device 392-1. Similarly, coherent light 490-2 is output by a light source of the optical device 392-2. The modulated coherent light generated from interference of feedback light with coherent light 490-2 is received by a light sensor of the optical device 392-2. The light sensor of the optical device 392-2 generates one or more signals based on the received (e.g., detected) modulated coherent light. Information regarding eye movement (e.g., movement of a portion 796-2 of the eye 340) along the y-direction can be determined using the one or more signals generated by the light sensor of optical device 392-2.

Thus, the use of two or more optical devices allows for enhanced movement sensing due to the different relative distances between the eye 340 and the light sensor of each optical device. As the eye is not a perfect sphere, three or more absolute distance measurements may be used to determine the absolute eye position in addition to accurately tracking eye movement (e.g., pupil movement) in three dimensions.

Figure 8A:
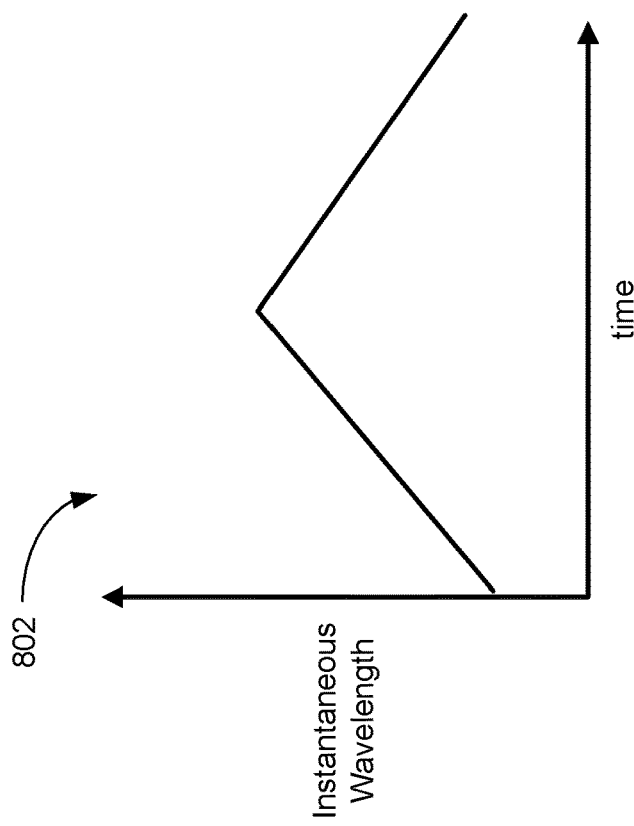
FIG. 8A illustrates input current and instantaneous wavelength of light output from a light source in accordance with some embodiments.
Figure 8A:
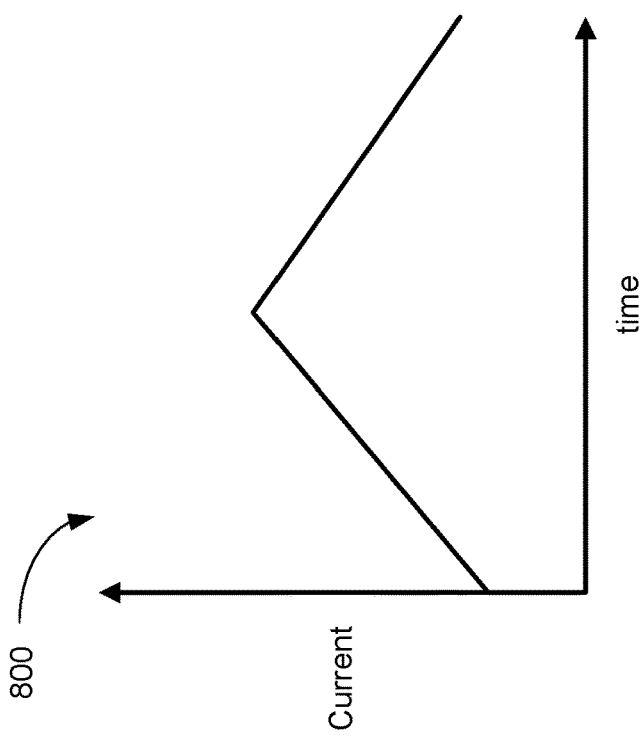
Figure 8B:
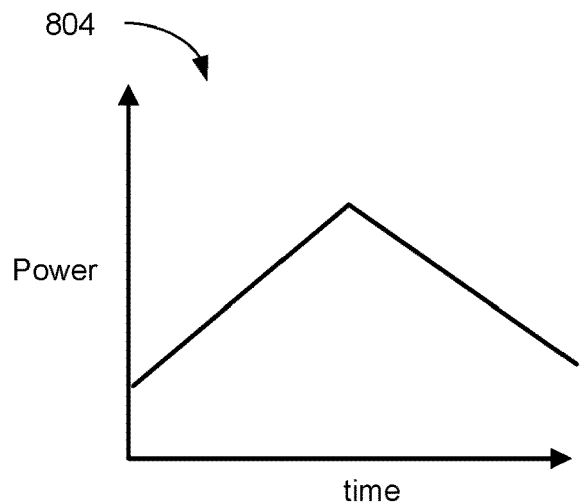
FIG. 8B illustrates a power profile of coherent light in accordance with some embodiments.
Figure 8B:
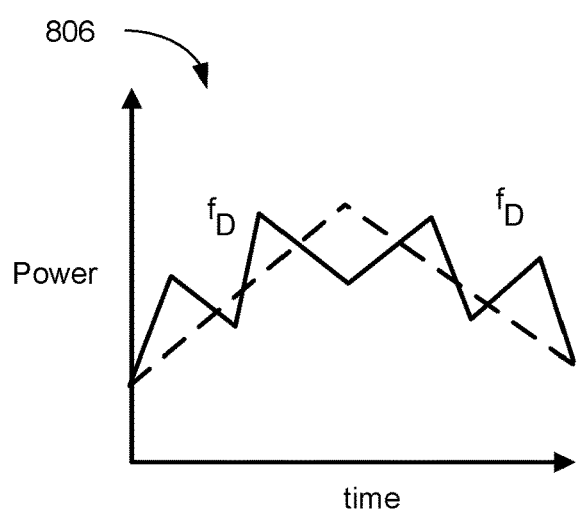
Figure 8B:
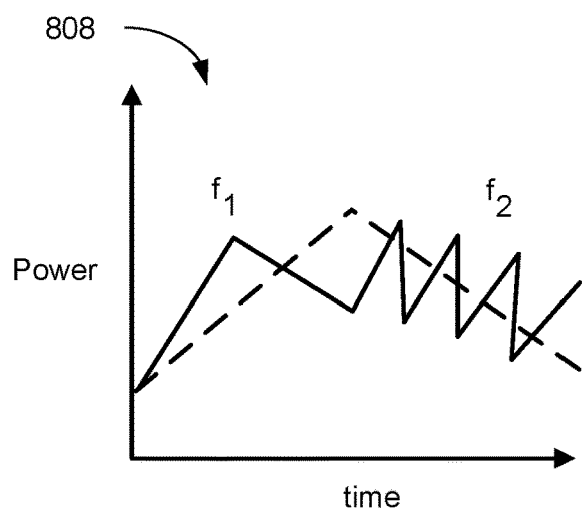

In some embodiments, the coherent light 490 output from the light source has a constant power (e.g., constant intensity) and a constant wavelength. In some embodiments, the coherent light 490 output from the light source does not have a constant power (e.g., a non-constant intensity). FIGS. 8A and 8B illustrate the benefits of providing coherent light 490 at a non-constant power.

FIG. 8A illustrates the effect of input current on an instantaneous wavelength of coherent light output from a light source in accordance with some embodiments. In some embodiments, a light source of an optical device (e.g., a light source 410 of an optical device 400) is coupled to a current source (e.g., electrical source 396 shown in FIG. 3B) that is configured to control output of the coherent light from the light source by changing an input current (e.g., electrical current) supplied to the light source. The current source may be configured to provide an input current having a pre-defined pattern. In some embodiments, the predefined pattern is a periodic pattern. In some embodiments, the pre-defined pattern is a non-uniform pattern.

Graph 800 of FIG. 8A illustrates an example where the current source provides an input current having a periodic (e.g., cyclical) pattern that is a triangular waveform. The light source outputs the coherent light in accordance with the received input current. In some embodiments, a change in the magnitude of the input current results in a shift in the instantaneous wavelength of the coherent light output from the light source. Graph 802 shows the instantaneous wavelength of the coherent light output from the light source in response to receiving the current as shown in graph 800. In this example, the instantaneous wavelength of the coherent light output from the light source increases with an increase in the input current and the instantaneous wavelength of the coherent light output from the light source decreases with a decrease in the input current.

FIG. 8B illustrates a detected power profile of coherent light in a light source in accordance with some embodiments. Graph 804 illustrates an example power profile of coherent light in a light source (e.g., coherent light 490 from light source 410) when the light source does not receive any feedback light (e.g., no back reflection). In the absence of the feedback light, the coherent light generated in the light source (e.g., generated in a cavity 416 of the light source 410) is not modulated by feedback light and thus, has a power profile that depends primarily on the profile (e.g., waveform) of the input current from the current source.

Graph 806 illustrates an example power profile of coherent light in the light source when feedback light (e.g., feedback light 492, which may include back-scattered-light or back-reflected light) is received from a static target (e.g., a stationary target, no eye-movement, no pupil movement). In this example, the power of the coherent light is modulated at a frequency, $f_D$. The modulation frequency, $f_D$, can be determined from power measurements or intensity measurements of the modulated coherent light (e.g., modulated coherent light 494). A distance (e.g., absolute distance, relative distance) between the light source and the target (e.g., distance between the light source 410 and the eye 340) can be calculated from (e.g., using) the modulation frequency, $f_D$. For example, the round-trip distance d (e.g., a sum of the distance from the light source to the target object and the distance from the target object to the light sensor) may be determined using the following equations:

$$f_D=(d\lambda/dI)\times(dI/dt)\times(d/\lambda^2) \text{ or}$$

$$d=(f_D\times\lambda^2)/[(d\lambda/dI)\times(dI/dt)]$$

where $\lambda$ is the wavelength and I is the current provided to the light source.

Graph 808 illustrates an example power profile of coherent light in the light source when feedback light (e.g., feedback light 492, back-scattered-light, back-reflected light) is received from a moving target (e.g., eye is moving, such as rotating). In this example, the power of the coherent light is modulated at changing frequencies over time such that a portion of the power corresponding to an increase in the input power is modulated at a first frequency, $f_1$, and a portion of the power corresponding to a decrease in the input power is modulated at a second frequency, $f_2$, that is different from the first frequency, $f_1$. A velocity of the moving target (e.g., a velocity of the eye 340 or a velocity of the pupil 350) can be calculated from (e.g., using) the modulation frequencies $f_1$ and $f_2$, and equations 1 and 2, shown below. In equations 1 and 2, $f_v$ is dependent on the velocity of the eye movement (e.g., pupil movement), as described above with respect to FIG. 7A.

$$f_1=f_D-f_v \qquad (1)$$

$$f_2=f_D+f_v \qquad (2)$$

Additionally, a distance (e.g., absolute distance, relative distance) between the light source and the target (e.g., distance between the light source 410 and the eye 340) can be calculated from (e.g., using) the modulation frequencies $f_1$ and $f_2$, using equation 3, shown below. As described above with respect to FIG. 7A, $f_D$ is dependent on the distance between the target (e.g., eye 340) and the light source.

$$f_D=0.5(f_1+f_2) \quad (3)$$

Thus, by changing the input current supplied to the light source, and thereby changing an instantaneous wavelength of the coherent light 490 output from the light source, an absolute distance of the target (e.g., eye 340 or pupil 350 of the eye 340) and the light source can be calculated (e.g., determined).

Figure 9A:
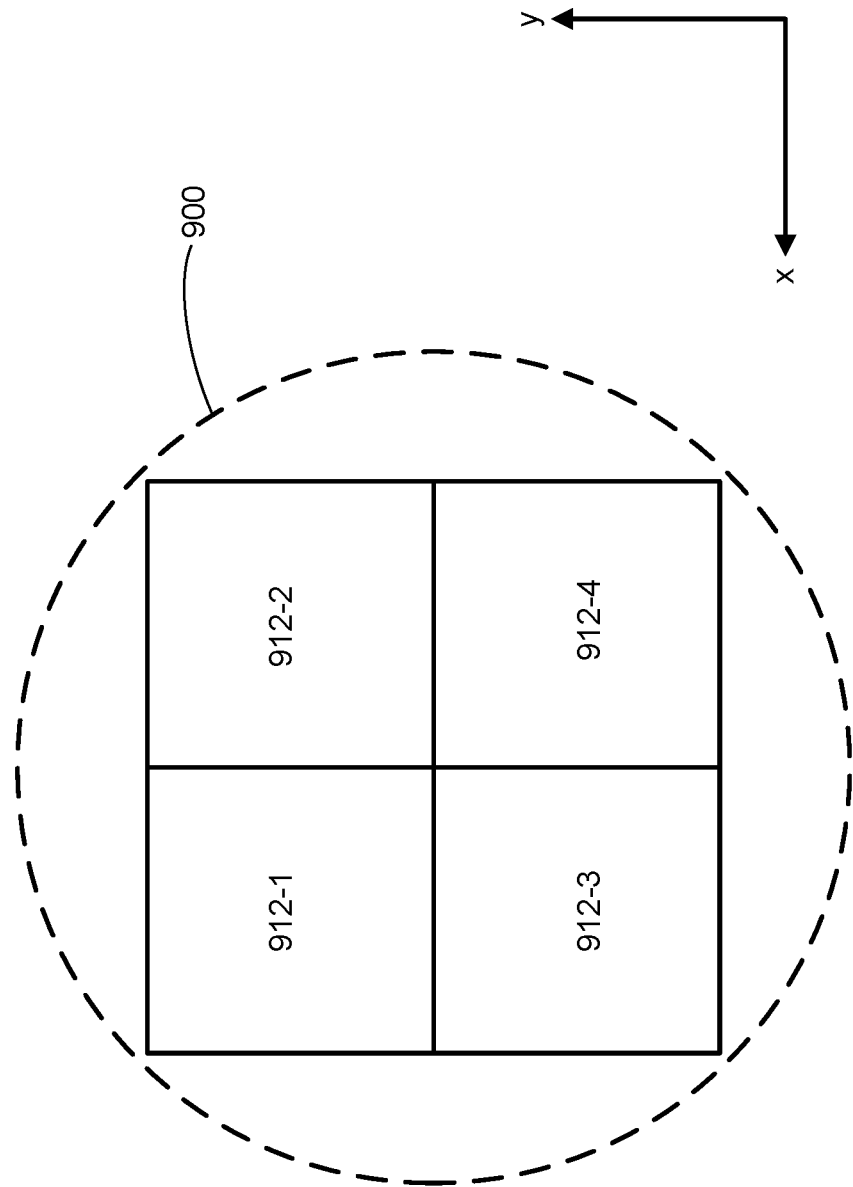
FIGS. 9A-9C are schematic diagrams illustrating an optical device that includes a plurality of light sources in accordance with some embodiments.
Figure 9B:
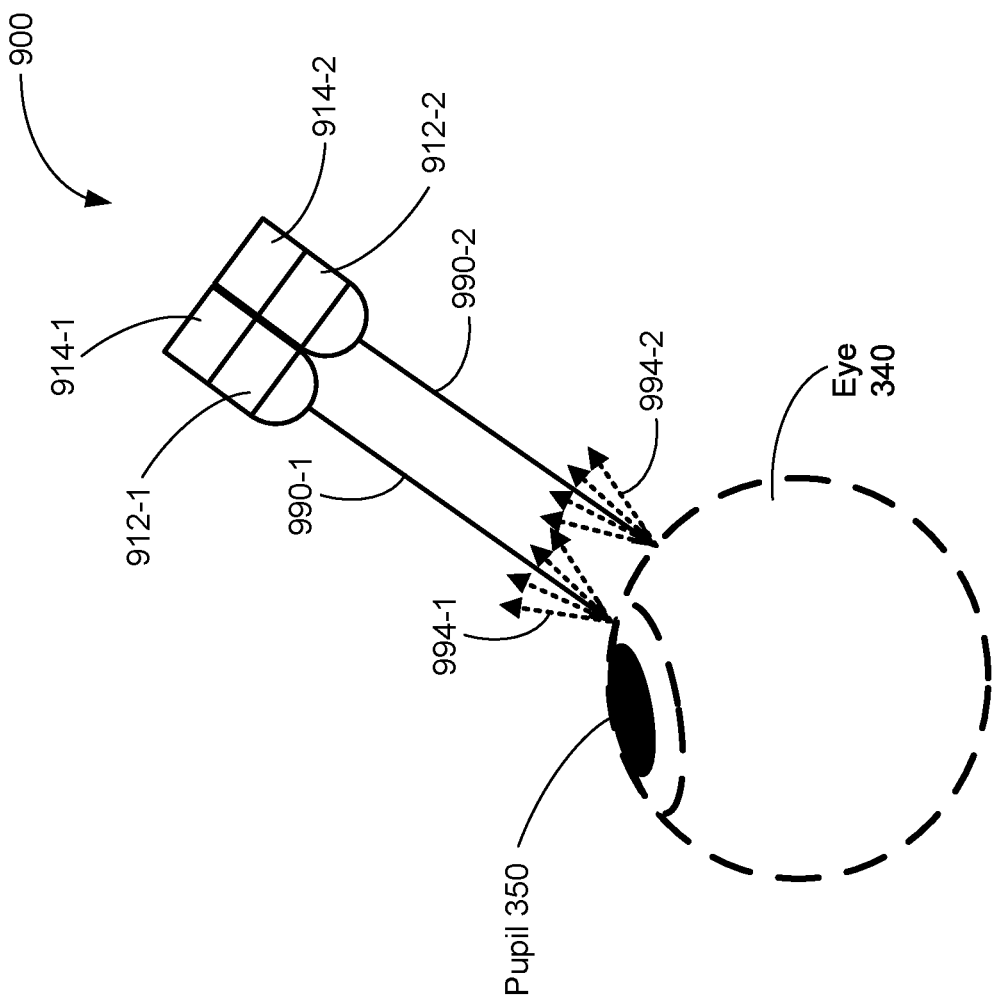
Figure 9C:
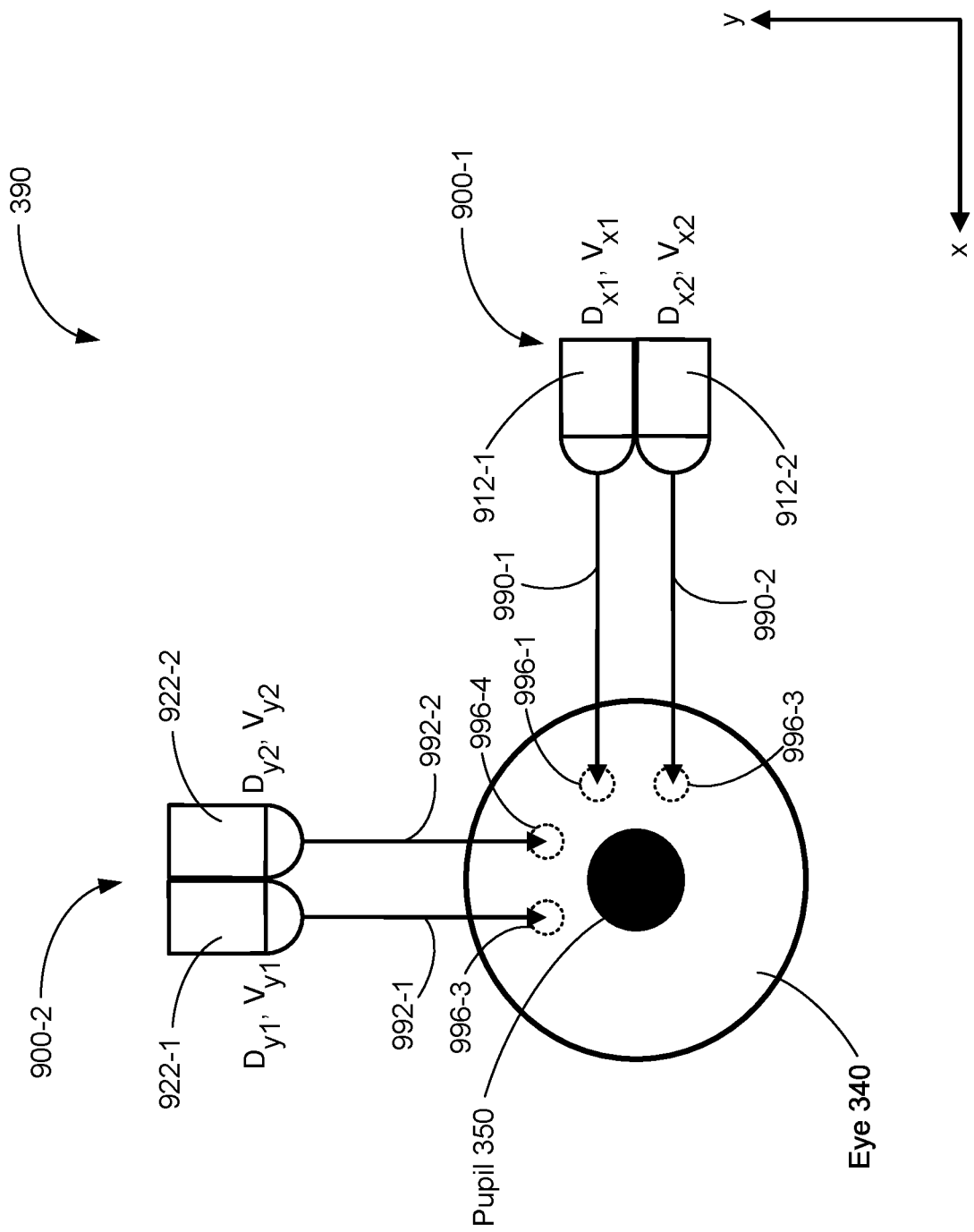

FIGS. 9A-9C are schematic diagrams illustrating an optical device 900 that includes a plurality of light sources and corresponding light sensors in accordance with some embodiments. The optical device 900 may be used in place of optical device 392 in FIG. 3B. Each of the light sources 912-1 to 912-4 shown in FIG. 9A has a corresponding light sensor (either external as shown in FIGS. 4A-4C or integrated as shown in FIGS. 5A, 5B, and 6A-6C). In FIG. 9A, the four light sources 912-1 to 912-4 are laterally arranged in a 2 by 2 matrix (e.g., arranged in a 2 by 2 matrix along the x and y directions). In configurations in which the light sensors are integrated light sensors (e.g., light sensors 520 and 620, integrated with their respective light source), the light sensors are also arranged in a 2 by 2 matrix. For example, the optical device 900 may include four light sources and four integrated light sensors that are arranged in a 2 by 2 matrix. Although FIG. 9A provides an example in which the optical device 900 includes four light sources and four light sensors, the optical device 900 may include any number of light sources and any number of sensors.

FIG. 9B shows an example of optical device 900 that includes a first light source 912-1 and a first vertically integrated light sensor 914-1 as well as a second light source 912-2 and a second vertically integrated light sensor 914-2. The light sources 912-1 and 912-2 are located at different spatial positions relative to the eye 340. Thus, a round trip optical path length of the light 990-1 output from the light source 912-1 toward the eye 340 and reflected or scattered back into the light source 912-1 (e.g., reflected or scattered back into a cavity of a light source of light source 912-1) as feedback light 994-1 is different from an optical path length of the light 990-2 output from the light source 912-2 toward the eye 340 and reflected or scattered back into the light source 912-2 (e.g., reflected or scattered back into a cavity of light source 912-2) as feedback light 994-2. The different round-trip optical path length of light corresponding to each light source of the optical device 900 provides additional information compared to an optical device that includes one light source. For example, at least because the eye 340 has a curved surface, light 990-1 and 994-1 form a first optical path that has a first distance and light 990-2 and 994-2 form a second optical path that has a second distance that is different from the first distance. Thus, one or more first signals generated by the light sensor 914-1 based on modulated light due to interference between light 990-1 and 994-1 is different from one or more second signals generated by the light sensor 914-2 based on modulated light due to interference between light 990-2 and 994-2. The optical device 900 may use the one or more first signals and the one or more second signals to determine additional information regarding movement of the eye 340 (or movement of the pupil 350 or the eye 340), such as a distance (e.g., relative distance, absolute distance) between the optical device 900 and the eye 340 (or the pupil 350 of the eye 340), and/or a velocity of pupil movement.

FIG. 9C is a schematic diagram illustrating an eye-tracking device 390 that includes a plurality of optical devices 900 in accordance with some embodiments. In FIG. 9C, the eye-tracking device 390 includes two optical devices, 900-1 and 900-2. Each of the optical devices 900-1 and 900-2 includes a plurality of light sources. The optical device 900-1 includes light sources 912-1 and 912-2 (and corresponding light sensors), and the optical device 900-2 includes light sources 922-1 and 922-2 (and corresponding light sensors). In some embodiments, the optical devices 900-1 and 900-2 are positioned such that light output from the respective optical devices are substantially perpendicular (e.g., orthogonal, forming a 90° angle) to each other. In some embodiments, the optical devices 900-1 and 900-2 are positioned such that the projections of light output from the respective optical devices on the x-y plane are substantially perpendicular (e.g., orthogonal, forming a 90° angle) to each other. For example, the optical device 900-1 is positioned such that coherent light 990-1 and 990-2 output from the light sources 912-1 and 912-2, respectively, are incident upon the eye 340 along the x-z plane. Optical device 900-2 is positioned such that coherent light 992-1 and 992-2 output from the light sources 922-1 and 922-2, respectively, are incident upon the eye 340 along the y-z plane.

Due to the differences in the distances and relative angles between the eye 340 and each light source 912-1, 912-2, 922-1, and 922-2, information received at each light sensor corresponding to each light source may provide independent distance and velocity information. For example, information obtained from a light sensor corresponding to the light source 912-1 provides information $D_{x1}$ and $V_{x1}$ corresponding to a first distance between the eye 340 (or a portion 996-1 thereof) and the light source 912-1 along the x-direction and a first velocity in the x-direction, respectively. Information obtained from a light sensor corresponding to the light source 912-2 provides information $D_{x2}$ and $V_{x2}$ corresponding to a second distance between the eye 340 (or a portion 996-2 thereof) and the light source 912-2 along the x-direction and a second velocity in the x-direction, respectively. Similarly, information obtained from a light sensor corresponding to the light source 922-1 provides information $D_{y1}$ and $V_{y1}$ corresponding to a third distance between the eye 340 (or a portion 996-3 thereof) and the light source 922-1 along the y-direction and a third velocity in the y-direction, respectively. Information obtained from a light sensor corresponding to the light source 922-2 provides information $D_{y2}$ and $V_{y2}$ corresponding to a fourth distance between the eye 340 (or a portion 996-4 thereof) and the light source 922-2 along the y-direction and a fourth velocity in the y-direction, respectively.

In some embodiments, the eye-tracking device 390 may include one or more additional optical components to direct the coherent light 490 output from the one or more light sources and/or to direct feedback light 492 toward the one or more light sources. FIGS. 10-13 illustrate examples of additional optical components that may be included in eye-tracking device 390.

Figure 10:
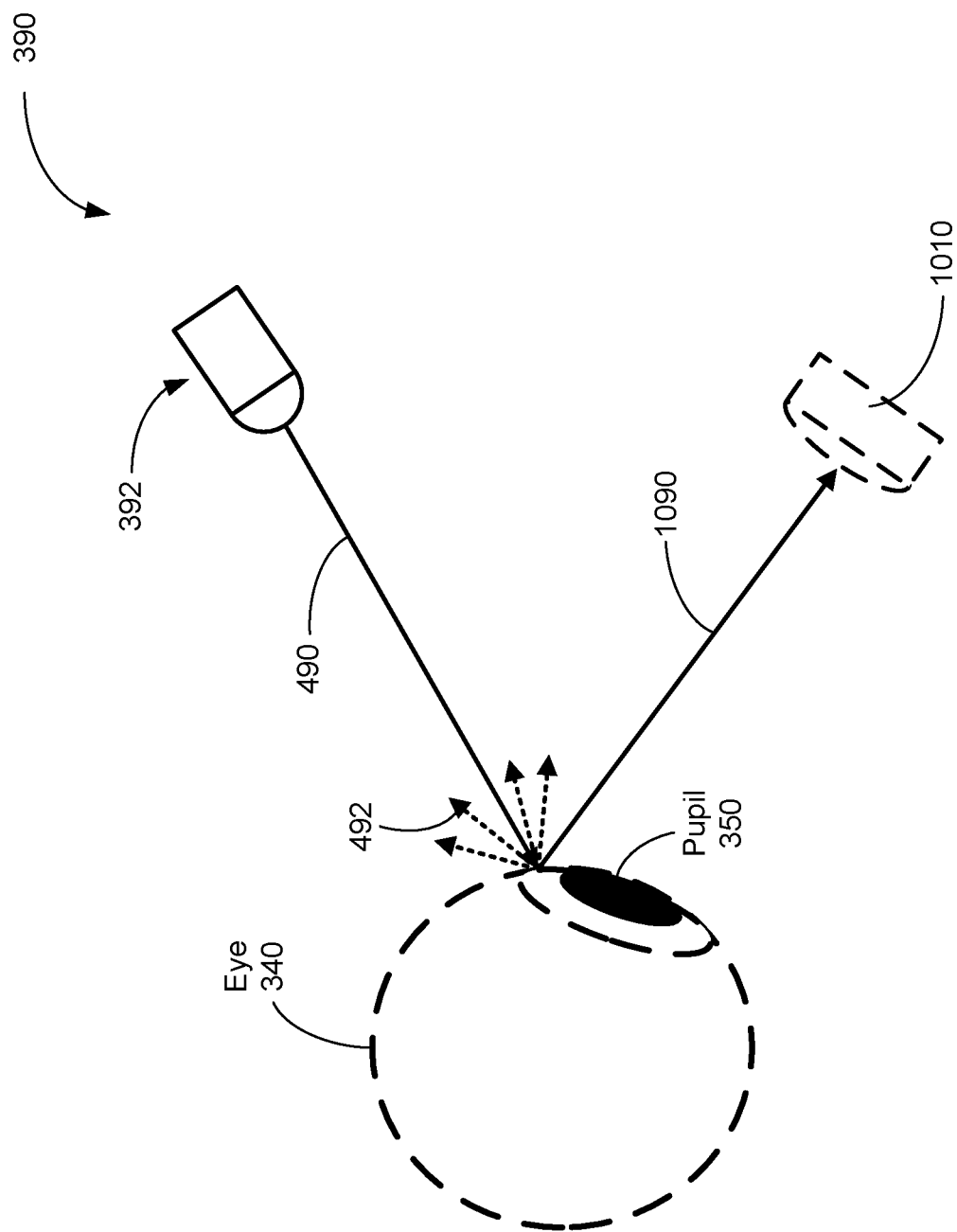
FIG. 10 is a schematic diagram illustrating an eye-tracking device that includes an imaging sensor in accordance with some embodiments.

In FIG. 10, eye-tracking device 390 includes an imaging sensor 1010. The imaging sensor 1010 is configured to (e.g., positioned to) receive (e.g., detect) at least a portion of the coherent light 490 output from the optical device 392 (e.g., from a light source of optical device 392) and reflected or scattered off the eye 340 as imaging light 1090. Information from the imaging light 1090 received at the imaging sensor 1010 is used to generate an image of the eye 340 (e.g., by the imaging sensor 1010 or a computing device that receives information from the imaging sensor 1010). Thus, in configurations in which the eye-tracking device 390 includes the imaging sensor 1010, the eye-tracking device 390 can produce an image of the eye 340 based on information obtained at the imaging sensor 1010 in addition to determining movement information regarding the eye 340 (or the pupil 350 of the eye 340) based on the one or more signals generated by a light sensor (e.g., light sensor 420, 520, 620) of optical device 392.

Figure 11A:
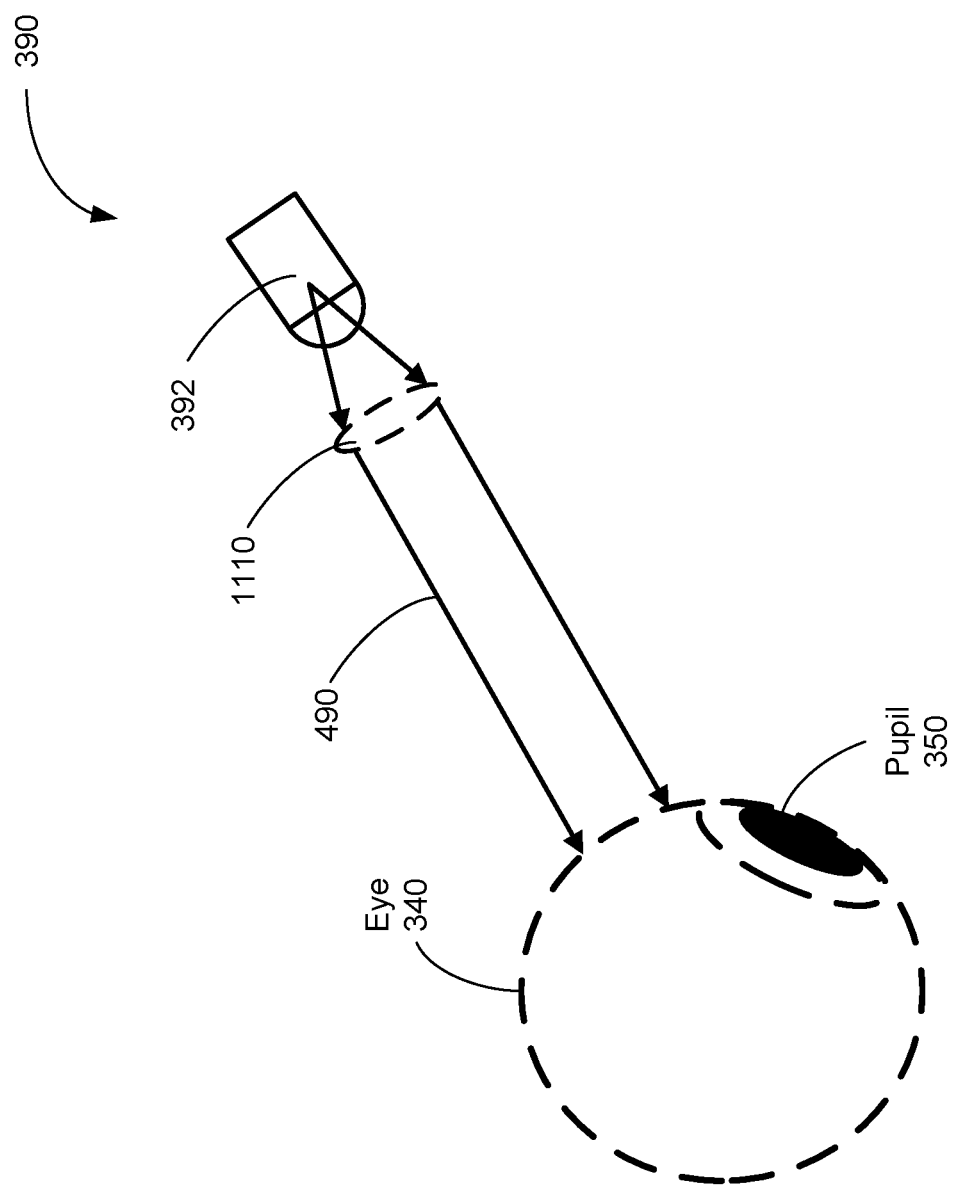
FIGS. 11A and 11B are schematic diagrams illustrating an eye-tracking device that includes a focusing optical component in accordance with some embodiments.
Figure 11B:
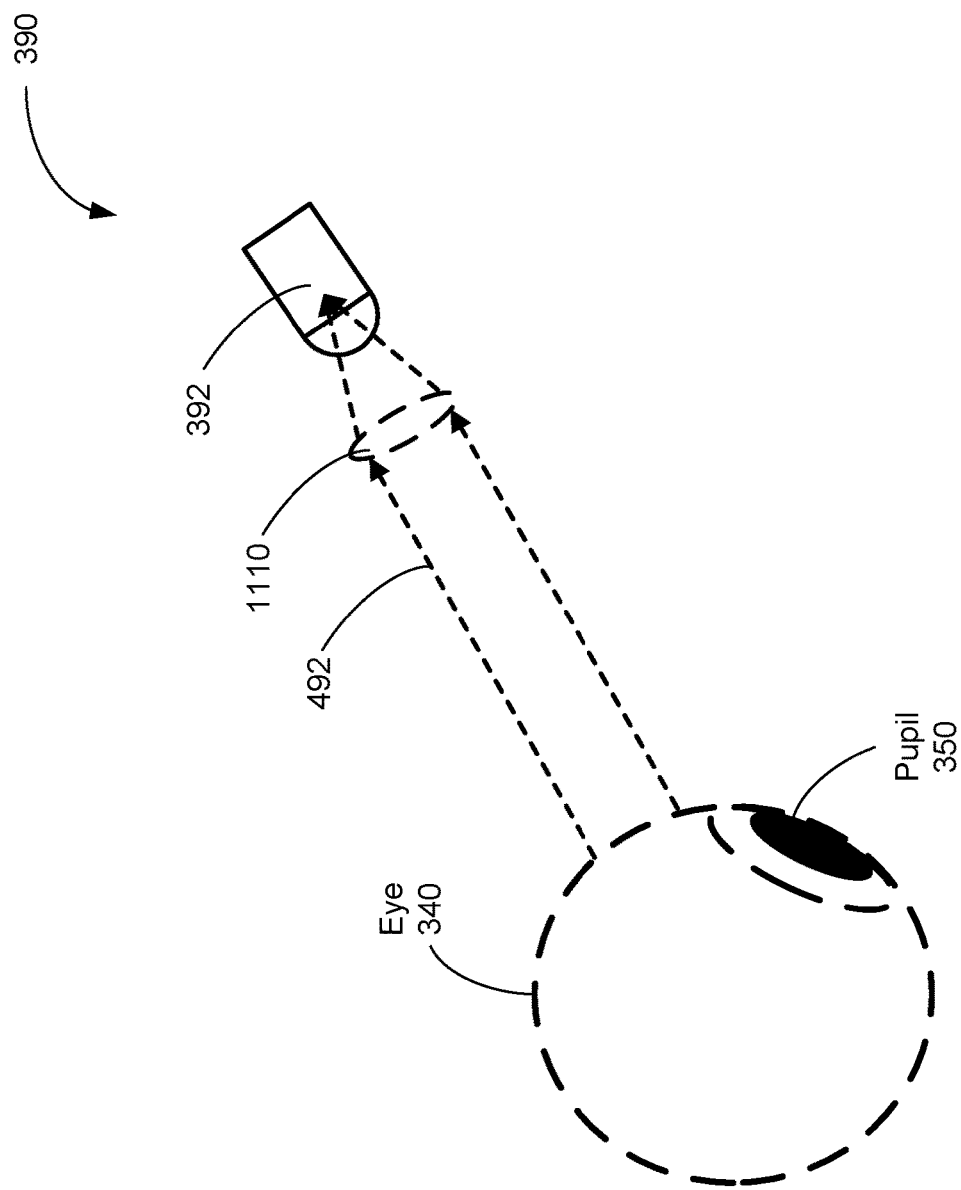

As shown in FIG. 11A-11B, the eye-tracking device 390 (e.g., eye-tracker) may include a focusing optical component 1110. In some embodiments, the focusing optical component 1110 is configured to (e.g., positioned to) receive the coherent light 490 output from the optical device 392 (e.g., from a light source of optical device 392) and collimate the coherent light 490 such that the coherent light 490 incident upon the eye 340 has a substantially collimated beam profile (e.g., low divergence). In some embodiments, the focusing optical component 1110 is also configured to (e.g., positioned to) receive feedback light 492 from the eye 340 and focus the feedback light 492 at a light source (or a cavity) of the optical device 392. Thus, the focusing optical component 1110 allows for improved efficiency in illuminating the eye 340 with the coherent light 490 as well as with collecting the feedback light 492 for transmission back into the optical device 392 (e.g., back into a cavity of a light source of the optical device 392), thereby increasing the signal detected by a light sensor (e.g., light sensor 420, 520, 620) of the optical device 392.

Figure 12:
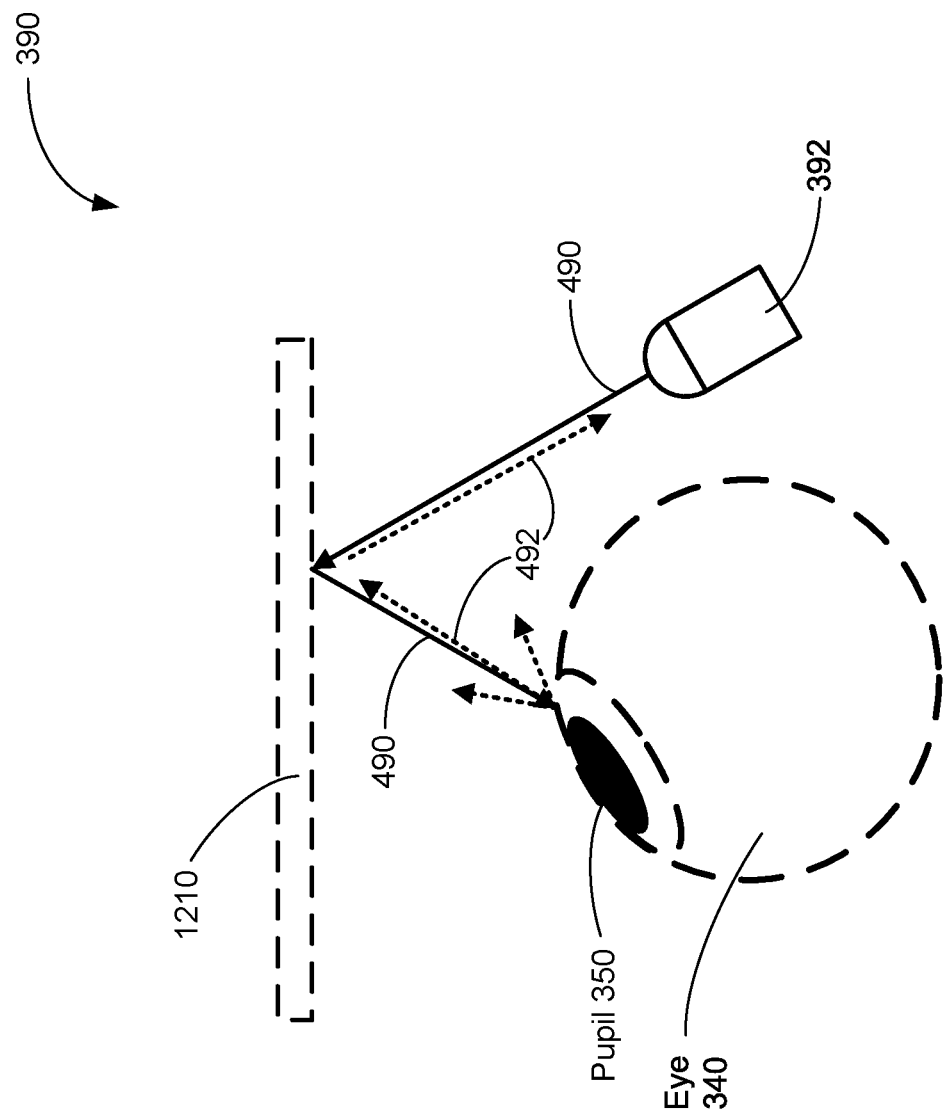
FIG. 12 is a schematic diagram illustrating an eye-tracking device that includes an optical component in accordance with some embodiments.

As shown in FIG. 12, the eye-tracking device 390 (e.g., eye-tracker) may include optical component 1210 in accordance with some embodiments. The optical component 1210 is configured to (e.g., positioned to) receive the coherent light 490 output from optical device 392 (e.g., output from a light source of the optical device 392) and redirect (e.g., reflect, refract) the coherent light 490 toward the eye 340 of the user. The optical component 1210 is also configured to (e.g., positioned to) receive feedback light 492 from the eye 340 and redirect (e.g., reflect, refract) the feedback light 492 toward the optical device 392. Thus, the optical component 1210 allows for flexible placement of the optical device 392. In some embodiments, the optical component 1210 is a waveguide (e.g., optical waveguide, optical fiber). In some embodiments, the optical component 1210 is a reflective or semi-reflective optical component, such as a mirror, a polarization sensitive mirror, or a partially reflective mirror. In some embodiments, the optical component 1210 is a refractive optical element such as a liquid crystal-based refractive optical element (e.g., a polarization volume hologram, a holographic optical element). In some embodiments, the optical component 1210 is a selectively reflective optical component (e.g., polarization selective, incident angle selective, wavelength selective) that can be placed in front of a display of a display device (e.g., a head-mounted display device). Thus, the overall footprint (or the size) of the eye-tracking device 390 may be reduced due to flexibility in the placement (e.g., location, position) of the optical device 392.

Figure 13A:
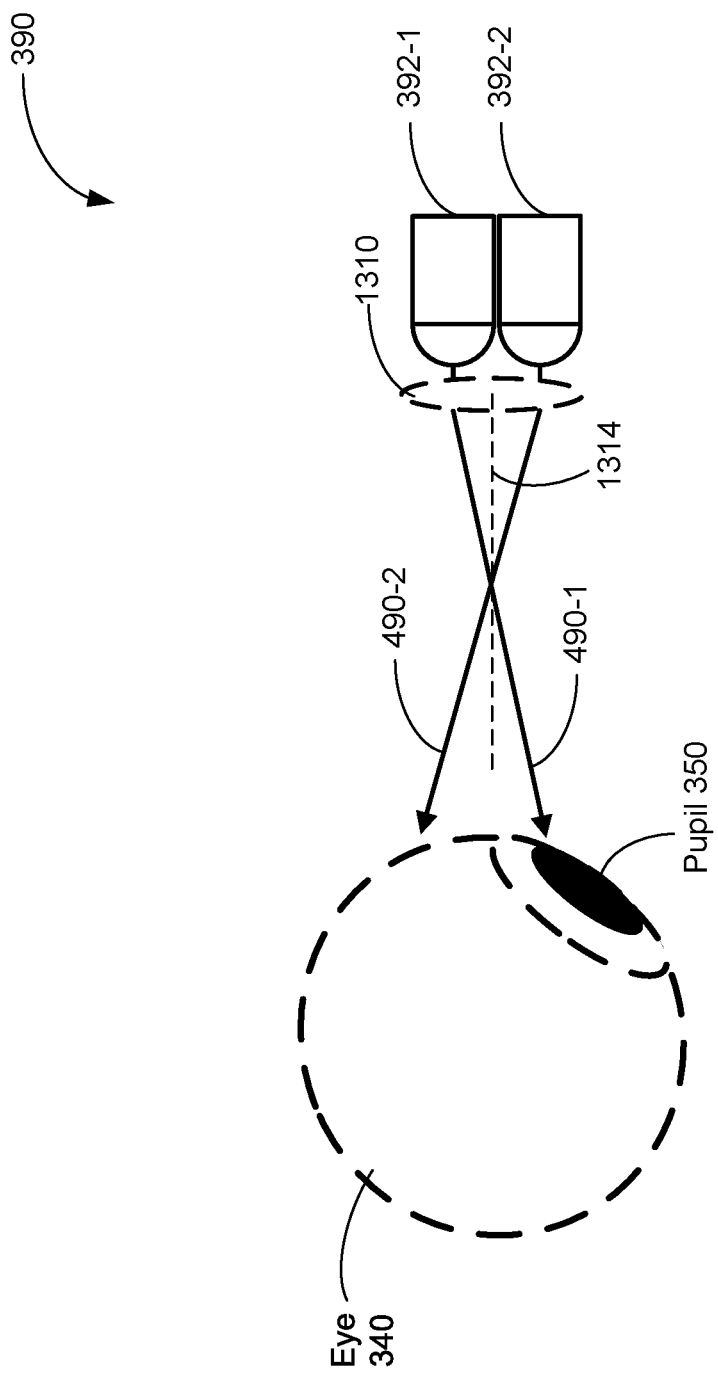
FIGS. 13A and 13B are schematic diagrams illustrating an eye-tracking device that includes an offset lens in accordance with some embodiments.
Figure 13B:
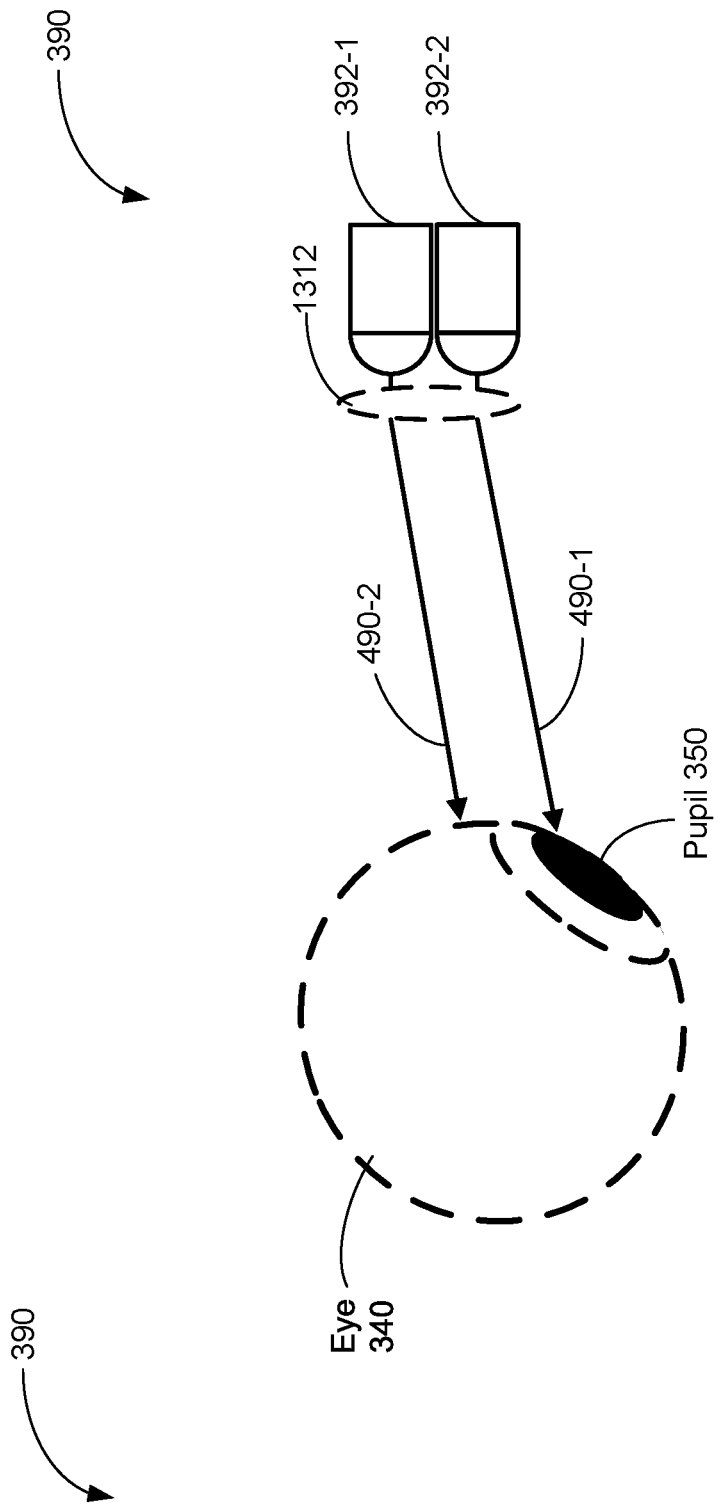

As shown in FIGS. 13A and 13B, the eye-tracking device 390 (e.g., eye-tracker) may include an offset lens (e.g., offset lens 1310 or 1312) in accordance with some embodiments. Referring to FIG. 13A, in some embodiments, the offset lens 1310 is configured to (e.g., positioned to) receive the coherent light 490-1 output from optical device 392-1 and steer the coherent light 490-1 in a first direction, and to receive the coherent light 490-2 output from the optical device 392-2 and steer the coherent light 490-2 in a second direction that is different from the first direction. In FIG. 13A, the first direction is on a first side of an optical axis 1314 of the offset lens 1310 and the second direction is on a second side, opposite to the first side, of the optical axis 1314 of the offset lens 1310. In some embodiments, the offset lens 1310 is disposed adjacent to an output port of optical devices 392-1 and 392-2 (e.g., an output port of a light source of the optical device 392-1 and an output port of a light source of the optical device 392-2).

Referring to FIG. 13B, in some embodiments, the offset lens 1312 is configured to (e.g., positioned to) receive coherent light 490-1 and coherent light 490-2 output from optical devices 392-1 and 392-2, respectively, and to steer the coherent light 490-1 and the coherent light 490-2 in a same direction. In some embodiments, the offset lens 1312 is disposed adjacent to an output port of optical devices 392-1 and 392-2 (e.g., an output port of a light source of the optical device 392-1 and an output port of a light source of the optical device 392-2).

FIGS. 14A and 14B are flow diagrams illustrating a method 1400 of detecting a movement of an eye 340 (or a pupil 350 of the eye 340) of a user in accordance with some embodiments. The method 1400 includes (operation 1410) outputting first coherent light (e.g., coherent light 490, 490-1, 990-1) from a first light source (e.g., light source 410, 912-1) of a first optical device 392 (including any of optical devices 400, 500, 600, 900) toward the eye. The first light source has a first cavity 416 and a first light sensor (e.g., light sensor 420, 520, 620, 914-1).

In some embodiments, the method 1400 also includes (operation 1412) changing, with an electrical source 396 coupled to the first light source 410, an electrical current provided to the first light source 410 in accordance with a predefined non-uniform pattern (e.g., the current profile shown in graph 800 of FIG. 8A).

The method 1400 also includes (operation 1420) receiving, at the first optical device 392, at least a portion of the first coherent light back from the eye 340 as feedback light 492. The feedback light 492 enters the first optical cavity 416 and causes modulation of an intensity of the first coherent light 490 (e.g., modulation of an intensity of coherent light generated inside the cavity 416). The method 1400 further includes (operation 1430) detecting the modulated intensity of the first coherent light (e.g., modulated coherent light 494) with the first light sensor, and (operation 1440) determining movement information of the eye 340 (or movement information of the pupil 350 of the eye 340) based on at least the modulated intensity of the first coherent light (e.g., intensity of the modulated coherent light 494) detected with the first light sensor.

In some embodiments, the method 1400 further includes (operation 1450) outputting second coherent light (e.g., coherent light 490-2) from a second light source of a second optical device 392-2 toward the eye 340. The second light source has a second optical cavity (e.g., cavity 416) and a second light sensor (e.g., light sensor 420, 520, 620). The method 1400 also includes (operation 1460) receiving, at the second optical device 392-2, at least a portion of the second coherent light 490-2 back from the eye 340 as feedback light 492-2. The feedback light 492-2 enters the second optical cavity (e.g., cavity 416 of second optical device 392-2) and causes modulation of an intensity of the second coherent light 490-2 (e.g., modulated coherent light). The method 1400 also includes (operation 1470) detecting the modulated intensity of the second coherent light (e.g., intensity of modulated coherent light) with the second light sensor (e.g., light sensor 420, 520, 620 of second optical device 392-2). The movement information is also determined based on the modulated intensity of the second coherent light (e.g., intensity of the modulated coherent light corresponding to coherent light 490-2) detected with the second light sensor.

In light of these principles, we now turn to certain embodiments of display devices.

In accordance with some embodiments, an eye-tracking device (e.g., eye-tracking device 390) includes a first optical device (e.g., optical device 392, 392-1, 900-1; including any of 400, 500, 600, 900) and one or more processors (e.g., processor(s) 394) coupled to the first optical device. The first optical device includes a first light source (e.g., light source 410, 912-1) with a first optical cavity (e.g., cavity 416). The first light source is positioned to output first coherent light (e.g., coherent light 490) toward an eye (e.g., eye 340) of a user and to receive at least a first portion of the first coherent light back from the eye of the user as feedback light (e.g., feedback light 492), whereby the feedback light enters the first optical cavity and causes modulation of an intensity of the first coherent light (e.g., self-mixing). The first optical device also includes a first light sensor (e.g., light sensor 420, 520, 620, 914-1) that is optically coupled with the first light source for detecting the modulated intensity of the first coherent light (e.g., modulated coherent light 494) and generating one or more first signals based on the detected intensity of the first coherent light. The one or more processors are configured for determining, from the one or more first signals, movement information of the eye of the user.

In some embodiments, the optical cavity (e.g., cavity 416) is defined by a first surface (e.g., surface 412) and a second surface (e.g., surface 414).

In some embodiments, the optical device includes a plurality of light sources and a plurality of sensors. For example, FIGS. 9A-9C show examples of optical device 900 that includes a plurality of light sources (e.g., light sources 912-1 and 912-2) and a plurality of sensors (corresponding to each of the light sources).

In some embodiments, the eye-tracking device (e.g., eye-tracking device 390) is configured to detect rapid eye movement of the pupil (e.g., pupil 350).

In some embodiments, the one or more processors (e.g., processor(s) 394) are coupled to the second optical device (e.g., optical device 392-2, 900-2) for determining, from the one or more second signals, the movement information of the eye (e.g., eye 340) of the user. In some embodiments, the one or more processors determine first movement information from the one or more first signals and second movement information from the one or more second signals, and determine the movement information based on the first movement information and the second movement information. In some embodiments, at least a first processor determines the first movement information and at least a second processor distinct and separate from the first processor determines the second movement information.

In some embodiments, the eye-tracking device (e.g., eye-tracking device 390) further includes a second optical device (e.g., optical device 392-2, 900-2) that is distinct and separate from the first optical device (e.g., optical device 392-1, 900-1). The second optical device includes a second light source with a second optical cavity (e.g., light source 410 and optical cavity 416 corresponding to second optical device 392-1, light source 922-1, 922-2). The second light source is positioned to output second coherent light (e.g., coherent light 490-2, 992-1, 992-2) toward the eye (e.g., eye 340) of the user and to receive at least a first portion of the second coherent light back from the eye of the user (e.g., second feedback light), whereby the received light enters the second optical cavity and causes modulation of an intensity of the second coherent light output from the second light source (e.g., modulated second coherent light). The second optical device also includes a second light sensor (e.g., light sensor 420, 520, 620 corresponding to the second optical device 392-2; a light sensor of 900-2) that is optically coupled with the second light source for detecting the modulated intensity of the second coherent light and generating one or more second signals based on the detected intensity of the second coherent light.

In some embodiments, the first optical device (e.g., optical device 392-1, 900-1) is positioned to provide the first coherent light (e.g., coherent light 490-1, 990-1 and 990-2) in a first direction (e.g., x-direction) and the second optical device (e.g., optical device 392-2, 900-2) is positioned to provide the second coherent light (e.g., coherent light 490-2, 990-3 and 990-4) in a second direction (e.g., y-direction) that is non-parallel to the first direction.

In some embodiments, the one or more second signals are different (e.g., distinct, independent, not coupled to) from the one or more first signals, and the one or more processors (e.g., processor(s) 394) are further configured to determine at least a velocity of the eye based on the one or more first signals and the one or more second signals.

In some embodiments, the first optical device (e.g., optical device 900) includes two or more light sources (e.g., light sources 912-1 to 912-4) with respective optical cavities (e.g., cavity 416 corresponding to each of light sources 912-1 to 912-4) arranged in an array (e.g., a 2 by 2 array as shown in FIG. 9A, a 2 by 1 array as shown in FIG. 9B).

In some embodiments, the first optical device (e.g., optical device 900) includes four light sources arranged in a 2 by 2 matrix.

In some embodiments, the eye-tracking device (e.g., eye-tracking device 390) further includes an optical element (e.g., offset lens 1310) that is optically coupled with the two or more light sources (e.g., light sources of optical devices 392-1 and 392-2) for steering the first coherent light (e.g., coherent light 490-1) from the first light source in a first direction and for steering coherent light (e.g., coherent light 490-2) from another light source of the two or more light sources in a second direction that is distinct from the first direction. For example, the optical element may be optically coupled with the two or more light sources so that the optical element steers light from the first light source in a first direction and light from the second light source in a different direction. In some embodiments, the optical element may be coupled to two or more light sources that belong to a same optical device. For example, an optical device (such as optical device 900 shown in FIGS. 9A-9C) may include a plurality of light sources (such as light sources 912-1 and 912-2) and the optical element may be optically coupled to the plurality of light sources belonging to a same optical device (e.g., offset lens 1310 may be optically coupled to an output of light sources 912-1 and 912-2).

In some embodiments, the eye-tracking device (e.g., eye-tracking device 390) further includes an optical element (e.g., offset lens 1312) that is optically coupled with the two or more light sources (e.g., light sources of optical devices 392-1 and 392-2) for steering the first coherent light (e.g., coherent light 490-1) and the second coherent light (e.g., coherent light 490-2) from two light different sources of the two or more light sources in a same direction. In some embodiments, the optical element may be coupled to two or more light sources that belong to a same optical device. For example, an optical device (such as optical device 900 shown in FIGS. 9A and 9B) may include a plurality of light sources (such as light sources 912-1 and 912-2) and the optical element may be optically coupled to the plurality of light sources belonging to a same optical device (e.g., offset lens 1312 may be optically coupled to an output of light sources 912-1 and 912-2) such that light output from the light sources of a same optical device are directed by offset lens 1312 in a same direction.

In some embodiments, the eye-tracking device further includes an electrical source (e.g., electrical source 396) that is coupled to the first light source for providing an electrical current with a predefined non-uniform pattern. For example, as shown in FIG. 8A, an electrical source may provide a periodic (e.g., saw-tooth, triangular) waveform to the first light source.

In some embodiments, modulation of the coherent light (e.g., coherent light 490) by the feedback light (e.g., feedback light 492) is independent of the modulation of the coherent light output from the light source (e.g., light source 410) by the electrical source (e.g., electrical source 396). For example, modulation of the intensity of coherent light by changing an input current provided by the electrical source happens at a first frequency, and modulation by the feedback light happens at a second frequency distinct from the first frequency.

In some embodiments, the one or more processors (e.g., processor(s) 394) are configured to determine frequencies (e.g., frequencies $f_1$ and $f_2$) of the intensity modulation for a rising intensity (e.g., increase in power shown in graph 806) and a falling intensity (e.g., decrease in power shown in graph 806) and determine a direction of a movement of the eye relative to a direction of the first coherent light from the first optical device (e.g., using equations 1 and 2).

In some embodiments, the one or more processors (e.g., processor(s) 394) are configured to determine a distance to the eye (e.g., eye 340) of the user along a direction (e.g., x-direction) of the first coherent light (e.g., coherent light 490, 490-1) from the first optical device (e.g., optical device 400, 392-1). For example, a distance between the eye and the first optical device can be calculated using equation 3.

In some embodiments, the eye-tracking device (e.g., eye-tracking device 390) further includes an imaging sensor (e.g., imaging sensor 1010) positioned for receiving at least a second portion of the first coherent light back from the eye (e.g., imaging light 1090). The eye-tracking device may generate an image of the eye based on the second portion of the first coherent light received at the imaging sensor. The second portion of the first coherent light is distinct from the first portion of the first coherent light (e.g., feedback light 492).

In some embodiments, the first light sensor (e.g., external light sensor 420) is distinct and separate from the first light source (e.g., light source 410).

In some embodiments, the first light sensor (e.g., vertically integrated light sensor 520) is vertically integrated with the first light source (e.g., light source 410).

In some embodiments, the first light sensor (e.g., horizontally integrated light sensor 620) is laterally integrated with the first light source (e.g., light source 410).

In some embodiments, the eye-tracking device (e.g., eye-tracking device 390) further includes one or more optical components (e.g., focusing optical component 1110) positioned to collimate the first coherent light (e.g., coherent light 490) output from the first light source (e.g., light source 410).

In some embodiments, the one or more optical components (e.g., focusing optical component 1110) are further positioned to focus at least the first portion of the first coherent light back from the eye (e.g., feedback light 492) into the first optical cavity (e.g., cavity 416 of light source 410).

In some embodiments, the eye-tracking device (e.g., eye-tracking device 390) further includes one or more optical components (e.g., optical component 1210) positioned to direct (e.g., steer, reflect, refract, guide) the first coherent light (e.g., coherent light 490) toward the eye (e.g., eye 340). In some embodiments, the eye of the user is not disposed along an optical axis of the first light source.

In accordance with some embodiments, a head-mounted display device (e.g., head-mounted display device 100, 300) that include an eye-tracking device (e.g., eye-tracking device 390) and a display (e.g., light emission device 310) configured to transmit one or more images to the eye (e.g., eye 340) of the user.

In some embodiments, the display outputs display light that corresponds to the one or more images and has one or more first wavelengths. In some embodiments, coherent light (e.g., coherent light 490) output from one or more light sources of the eye-tracking device (e.g., eye-tracking device 390) have a wavelength that is different from the one or more first wavelengths of the display light. In some embodiments, wavelengths of the coherent light output from one or more light sources of the eye-tracking device do not overlap with the one or more first wavelengths of the display light.

In accordance with some embodiments, an eye-tracking device (e.g., eye-tracking device 390) includes a first optical device (e.g., optical device 392, 392-1, 900-1; including any of 400, 500, 600, 900) and one or more processors (e.g., processor(s) 394) coupled to the first optical device. The first optical device includes a first light source (e.g., light source 410, 912-1) with a first optical cavity (e.g., cavity 416). The first light source is positioned to output first coherent light (e.g., coherent light 490) toward an eye (e.g., eye 340) of a user and to receive at least a first portion of the first coherent light back from the eye of the user as feedback light (e.g., feedback light 492), whereby the feedback light enters the first optical cavity and causes modulation of an intensity of the first coherent light (e.g., self-mixing). The first optical device also includes a first light sensor (e.g., light sensor 420, 520, 620, 914-1) that is optically coupled with the first light source for detecting the modulated intensity of the first coherent light (e.g., modulated coherent light 494) and generating one or more first signals based on the detected intensity of the first coherent light. The one or more processors are configured for determining, from the one or more first signals, a distance to the eye of the user along a direction of the first coherent light from the first optical device.

In accordance with some embodiments, a method (e.g., method 1400) of detecting a movement of an eye (e.g., eye 340) of a user includes (operation 1410) outputting first coherent light (e.g., coherent light 490) from a first light source (e.g., light source 410) of a first optical device (e.g., optical device 392, 392-1, 900-1) toward the eye. The first light source has a first optical cavity (e.g., cavity 416) and the first optical device also includes a first light sensor (e.g., light sensor 420, 520, 620, 914-1). The method also includes (operation 1420) receiving, at the first optical device, at least a portion of the first coherent light back from the eye as feedback light (e.g., feedback light 492), whereby the feedback light enters the first optical cavity and causes modulation of an intensity of the first coherent light. The method further includes (operation 1430) detecting the modulated intensity of the first coherent light with the first light sensor and (operation 1440) determining movement information of the eye based on at least the modulated intensity of the first coherent light detected with the first light sensor.

In some embodiments, the method further includes (operation 1412) changing, with an electrical source (e.g., electrical source 396) coupled to the first light source (e.g., light source 410), an electrical current provided to the first light source in accordance with a predefined non-uniform pattern (e.g., electric current corresponding to a periodic function, shown in FIG. 8A).

In some embodiments, the method further includes (operation 1450) outputting second coherent light (e.g., coherent light 490-2, 992-1, 992-2) from a second light source (e.g., light source 922-1 or 922-2) of a second optical device (e.g., optical device 392-2, 900-2) toward the eye. The second light source has a second optical cavity (e.g., cavity 416) and the second optical device also includes a second light sensor (e.g., light sensor 420, 520, 620). The method also includes (operation 1460) receiving, at the second optical device, at least a portion of the second coherent light back from the eye as feedback light (e.g., second feedback light), whereby the feedback light enters the second optical cavity and causes modulation of an intensity of the second coherent light. The method further includes (operation 1470) detecting the modulated intensity of the second coherent light with the second light sensor. The movement information is also determined based on the modulated intensity of the second coherent light detected with the second light sensor.

In some embodiments, the method (e.g., method 1400) also includes applying a high pass filter (e.g., an electrical high pass filter) to extract high frequency components of the one or more first signals and/or the one or more second signals. A relative position of the pupil is determined based on at least the high frequency components of the one or more first signals and/or the one of more second signals.

In accordance with some embodiments, a method (e.g., method 1400) of detecting a movement of an eye (e.g., eye 340) of a user includes (operation 1410) outputting first coherent light (e.g., coherent light 490) from a first light source (e.g., light source 410) of a first optical device (e.g., optical device 392, 392-1, 900-1) toward the eye. The first light source has a first optical cavity (e.g., cavity 416) and the first optical device also includes a first light sensor (e.g., light sensor 420, 520, 620, 914-1). The method also includes (operation 1420) receiving, at the first optical device, at least a portion of the first coherent light back from the eye as feedback light (e.g., feedback light 492), whereby the feedback light enters the first optical cavity and causes modulation of an intensity of the first coherent light. The method further includes (operation 1430) detecting the modulated intensity of the first coherent light with the first light sensor and determining a distance to the eye along a direction of the first coherent light from the first optical device based on at least the modulated intensity of the first coherent light detected with the first light sensor.

Although various drawings illustrate operations of particular components or particular groups of components with respect to one eye, a person having ordinary skill in the art would understand that analogous operations can be performed with respect to the other eye or both eyes. For brevity, such details are not repeated herein.

Although some of various drawings illustrate a number of logical stages in a particular order, stages which are not order dependent may be reordered and other stages may be combined or broken out. While some reordering or other groupings are specifically mentioned, others will be apparent to those of ordinary skill in the art, so the ordering and groupings presented herein are not an exhaustive list of alternatives. Moreover, it should be recognized that the stages could be implemented in hardware, firmware, software or any combination thereof.

The foregoing description, for purpose of explanation, has been described with reference to specific embodiments. However, the illustrative discussions above are not intended to be exhaustive or to limit the scope of the claims to the precise forms disclosed. Many modifications and variations are possible in view of the above teachings. The embodiments were chosen in order to best explain the principles underlying the claims and their practical applications, to thereby enable others skilled in the art to best use the embodiments with various modifications as are suited to the particular uses contemplated.

What is claimed is:

1. An eye-tracking device, comprising:
   a first optical device including:
      a first light source with a first optical cavity, the first light source positioned to:
         output first coherent light toward an eye of a user; and
         receive at least a first portion of the first coherent light back from the eye of the user as feedback light, whereby the feedback light enters the first optical cavity and causes modulation of an intensity of the first coherent light; and
      a first light sensor optically coupled with the first light source for detecting the modulated intensity of the first coherent light and generating one or more first signals based on the detected intensity of the first coherent light;
   one or more processors coupled to the first optical device for determining, from the one or more first signals, movement information of the eye of the user; and
   a second optical device distinct and separate from the first optical device, the second optical device including:
      a second light source with a second optical cavity, the second light source positioned to:
         output second coherent light toward the eye of the user; and
         receive at least a first portion of the second coherent light back from the eye of the user, whereby the received light enters the second optical cavity and causes modulation of an intensity of the second coherent light output from the second light source; and
      a second light sensor optically coupled with the second light source for detecting the modulated intensity of the second coherent light and generating one or more second signals based on the detected intensity of the second coherent light.

2. The eye-tracking device of claim 1, wherein:
   the first optical device is positioned to provide the first coherent light in a first direction; and
   the second optical device is positioned to provide the second coherent light in a second direction that is non-parallel to the first direction.

3. The eye-tracking device of claim 1, wherein:
   the one or more second signals are different from the one or more first signals; and
   the one or more processors are further configured to determine at least a velocity of the eye based on the one or more first signals and the one or more second signals.

4. The eye-tracking device of claim 1, wherein:
the first optical device includes two or more light sources with respective optical cavities arranged in an array.

5. The eye-tracking device of claim 4, further comprising:
an optical element optically coupled with the two or more light sources for steering the first coherent light from the first light source in a first direction and coherent light from another light source of the two or more light sources in a second direction that is distinct from the first direction.

6. The eye-tracking device of claim 1, further comprising:
an electrical source coupled to the first light source for providing an electrical current with a predefined non-uniform pattern.

7. The eye-tracking device of claim 6, wherein the one or more processors are configured to determine frequencies of the intensity modulation for a rising intensity and a falling intensity and determine a direction of a movement of the eye relative to a direction of the first coherent light from the first optical device.

8. The eye-tracking device of claim 6, wherein the one or more processors are configured to determine a distance to the eye of the user along a direction of the first coherent light from the first optical device.

9. The eye-tracking device of claim 1, further comprising:
an imaging sensor positioned for receiving at least a second portion of the first coherent light back from the eye and generating an image of the eye based on the received second portion of the first coherent light, wherein the second portion of the first coherent light is distinct from the first portion of the first coherent light.

10. The eye-tracking device of claim 1, wherein the first light sensor is distinct and separate from the first light source.

11. The eye-tracking device of claim 1, wherein the first light sensor is laterally integrated with the first light source.

12. The eye-tracking device of claim 1, wherein the first light sensor is vertically integrated with the first light source.

13. The eye-tracking device of claim 1, further comprising one or more optical components positioned to collimate the first coherent light output from the first light source.

14. The eye-tracking device of claim 13, wherein the one or more optical components are further positioned to focus at least the first portion of the first coherent light back from the eye into the first optical cavity.

15. The eye-tracking device of claim 1, further comprising one or more optical components positioned to direct the first coherent light toward the eye.

16. A head-mounted display device, comprising:
the eye-tracking device of claim 1; and
a display configured to transmit one or more images to the eye of the user.

17. The eye-tracking device of claim 1, wherein the one or more processors are also coupled to the second optical device for determining, also from the one or more second signals, the movement information of the eye of the user.

18. A method of detecting a movement of an eye of a user, the method comprising:
outputting first coherent light from a first light source of a first optical device toward the eye, wherein the first light source has a first optical cavity and the first optical device also includes a first light sensor;
receiving, at the first optical device, at least a portion of the first coherent light back from the eye as feedback light, whereby the feedback light enters the first optical cavity and causes modulation of an intensity of the first coherent light;
detecting, with the first light sensor, the modulated intensity of the first coherent light;
determining movement information of the eye based on at least the modulated intensity of the first coherent light detected with the first light sensor;
outputting second coherent light from a second light source of a second optical device toward the eye, wherein the second light source has a second optical cavity and the second optical device also includes a second light sensor;
receiving, at the second optical device, at least a portion of the second coherent light back from the eye as feedback light, whereby the feedback light enters the second optical cavity and causes modulation of an intensity of the second coherent light; and
detecting, with the second light sensor, the modulated intensity of the second coherent light, wherein the movement information is determined also based on the modulated intensity of the second coherent light detected with the second light sensor.

19. The method of claim 18, further comprising:
changing, with an electrical source coupled to the first light source, an electrical current provided to the first light source in accordance with a predefined non-uniform pattern.

* * * * *